(12) United States Patent
Jia

(10) Patent No.: US 11,369,653 B2
(45) Date of Patent: Jun. 28, 2022

(54) TRADITIONAL CHINESE MEDICINE COMPOSITION FOR TREATING CARDIOVASCULAR AND CEREBROVASCULAR DISEASE, PREPARATION METHOD THEREFOR AND USE THEREOF

(71) Applicant: Hongzhang Jia, Beijing (CN)

(72) Inventor: Hongzhang Jia, Beijing (CN)

(73) Assignee: Hongzhang Jia, Beijing (CN)

( * ) Notice: Subject to any disclaimer, the term of this patent is extended or adjusted under 35 U.S.C. 154(b) by 0 days.

(21) Appl. No.: 17/048,438

(22) PCT Filed: Jul. 23, 2018

(86) PCT No.: PCT/CN2018/096673
§ 371 (c)(1),
(2) Date: Oct. 16, 2020

(87) PCT Pub. No.: WO2019/200768
PCT Pub. Date: Oct. 24, 2019

(65) Prior Publication Data
US 2021/0161983 A1  Jun. 3, 2021

(30) Foreign Application Priority Data

Apr. 17, 2018 (CN) .......................... 201810346463.1

(51) Int. Cl.
| | |
|---|---|
| *A61K 36/236* | (2006.01) |
| *A61P 7/02* | (2006.01) |
| *A61P 9/10* | (2006.01) |
| *A61P 9/04* | (2006.01) |
| *A61K 9/00* | (2006.01) |
| *A61K 36/21* | (2006.01) |
| *A61K 36/46* | (2006.01) |
| *A61K 36/88* | (2006.01) |
| *A61K 36/9066* | (2006.01) |

(52) U.S. Cl.
CPC .......... *A61K 36/236* (2013.01); *A61K 9/0053* (2013.01); *A61K 36/21* (2013.01); *A61K 36/46* (2013.01); *A61K 36/88* (2013.01); *A61K 36/9066* (2013.01); *A61P 7/02* (2018.01); *A61P 9/04* (2018.01); *A61P 9/10* (2018.01); *A61K 2236/331* (2013.01); *A61K 2236/333* (2013.01); *A61K 2236/39* (2013.01); *A61K 2236/51* (2013.01)

(58) Field of Classification Search
None
See application file for complete search history.

(56) References Cited

U.S. PATENT DOCUMENTS

2008/0220084 A1 * 9/2008 Fan .................... A61K 36/8988
424/538

FOREIGN PATENT DOCUMENTS

| CN | 1197654 A | 11/1998 |
|---|---|---|
| CN | 1457831 A | 11/2003 |
| CN | 1480160 A | 3/2004 |
| CN | 1679832 A | 10/2005 |
| CN | 1788785 A | 6/2006 |
| CN | 1840149 A | 10/2006 |
| CN | 101474219 A | 7/2009 |
| CN | 102805760 A | 12/2012 |
| CN | 103007185 A | 4/2013 |
| CN | 103182012 A | 7/2013 |
| CN | 103623341 A * | 3/2014 |
| CN | 103638462 A | 3/2014 |
| CN | 103933474 A | 7/2014 |
| CN | 103990079 A | 8/2014 |
| CN | 104288464 A | 1/2015 |
| CN | 104491759 A * | 4/2015 |
| CN | 104873948 A | 9/2015 |
| CN | 105477380 A | 4/2016 |
| CN | 105878922 A * | 8/2016 |
| CN | 105920375 A | 9/2016 |
| JP | 2005516930 A | 6/2005 |

(Continued)

OTHER PUBLICATIONS

The Office Action issued by the China National Intellectual Property Administration (CNIPA) dated Jun. 29, 2020 for the Chinese Patent Application No. 201810346463.1.

Cai, et al., Journal of Shanxi Traditional Chinese Medicine, 23(2), 2002 (the cited reference (Nonpatent 1) in the Office Action issued by the CNIPA dated Jun. 29, 2020 for the Chinese Patent Application No. 201810346463.1, p. 10, first reference).

Cao et al., Journal of Shanxi Traditional Chinese Medicine, 38(4), Apr. 2017 (the cited reference (Nonpatent 2) in the Office Action issued by the CNIPA dated Jun. 29, 2020 for the Chinese Patent Application No. 201810346463.1, p. 10, second reference).

(Continued)

*Primary Examiner* — Susan Hoffman
(74) *Attorney, Agent, or Firm* — Maschoff Brennan; Brent A. Johnson; Yuefen Zhou

(57) ABSTRACT

A traditional Chinese medicine composition for treating cardiovascular and cerebrovascular disease, the active ingredients thereof being composed of: 1) an ethanol extract of 6-12 parts of *Ligusticum wallichii* and 5-10 parts of Curcumae Radix, and 2) an aqueous extract of extract residue of the described *Ligusticum wallichii* and Curcumae Radix and 5-10 parts of Radix Cyathulae; the traditional Chinese medicine composition may further comprise an aqueous extract of 5-10 parts of *Allium macrostemon* and 6-12 parts of *Eucommia ulmoides*. The traditional Chinese medicine composition relates to medicine made from plant compounds, and has significant medicinal effects on myocardial contraction disorder and myocardial dilation disorder, platelet aggregation thrombosis and myocardial ischemia, myocardial hypoxia, myocardial fatigue, and so on, being particularly suitable for treating coronary heart disease and chronic or acute heart failure.

13 Claims, 4 Drawing Sheets

(56) References Cited

FOREIGN PATENT DOCUMENTS

JP          2016503040 A      2/2016

OTHER PUBLICATIONS

Chen, Journal of Hubei College of TCM, 3(1), Dec. 2001 (the cited reference (Nonpatent 3) in the Office Action Issued by the CNIPA dated Jun. 29, 2020 for the Chinese Patent Application No. 201810346463.1, p. 10, third reference).

Yang, Journal of Practical Traditional Chinese Internal Medicine, 29(10), Jan. 2015 (the cited reference Nonpatent 4) in the Office Action issued by the CNIPA dated Jun. 29, 2020 for the Chinese Patent Application No. 201810346463.1, p. 10, fourth reference).

Guo et al., Chinese Journal of Integrative Medicine on Cardio-/Cerebrovascular Disease, 14(22), Nov. 2016 (the cited reference (Nonpatent 5) in the Office Action issued by the CNIPA dated Jun. 29, 2020 or the Chinese Patent Application No. 201810346463.1, p. 10, fifth reference).

International Search Report and Written Opinion for PCT/CN2018/096673, dated Jan. 17, 2019.

Hansen et al., Heterogeneity of insulin responses: phases leading to Type 2 (non-insulin-dependent) diabetes mellitus in the rhesus monkey, Diabetologia, 29, 713-719, bearing an alleged date of Oct. 1986.

Nagueh et al., Recommendation for the Evaluation of Left Ventricular Diastolic Function by Echocardiography, American Society of Echocardiography, 22(2), 107-133, bearing an alleged date of Feb. 2009.

Solomon et al., The angiotensin receptor neprilysin inhibitor LCZ696 in heart failure with preserved ejection fraction: a phase 2 double-blind randomised controlled trial, Lancet, 380, 1387-1395, bearing an alleged date of Oct. 2012.

Qian et al., Diastolic dysfunction in spontaneous type 2 diabetes rhesus monkeys: a study using echocardiography and magnetic resonance imaging, BMC Cardiovascular Disorders, 15(59), 1-14, bearing an alleged date of Jun. 2015.

Jeong, et al., Role of Mitochondrial Oxidative Stress in Glucose Tolerance, Insulin Resistance, and Cardiac Diastolic Dysfunction, Journal of the American Heart Association, 5(5) 1-18, bearing an alleged date of May 2016.

The Notification to Grant Patent Right for Invention issued by the China National Intellectual Property Administration (CNIPA) dated Mar. 17, 2021 for the Chinese Patent Application No. 201810346463.1.

Extended European Search Report dated May 4, 2021 for the European Patent Application No. 18915303.4.

The first Office Action issued by the Japanese Patent Office dated Oct. 5, 2021 for the Japanese Patent Application No. 2020-557255.

\* cited by examiner

TRADITIONAL CHINESE MEDICINE COMPOSITION FOR TREATING CARDIOVASCULAR AND CEREBROVASCULAR DISEASE, PREPARATION METHOD THEREFOR AND USE THEREOF

CROSS-REFERENCE TO RELATED APPLICATIONS

This application is a National phase of International Application No. PCT/CN2018/096673, filed Jul. 23, 2018, which claims priority to Chinese Patent Application No. 201810346463.1, filed Apr. 17, 2018, both of which are hereby incorporated by reference in their entireties.

TECHNICAL FIELD

The present disclosure belongs to the field of drug research and development, and in particular the present disclosure relates to a Traditional Chinese Medicine composition for treatment of cardiovascular or cerebrovascular diseases and its preparation method.

BACKGROUND

Cardiovascular and cerebrovascular diseases represent a serious threat to human health, especially the elderly over 50 years old. The diseases are characterized by high morbidity, high disability and high mortality. According to epidemiological survey in China, incidence rate and mortality rate of cardiovascular and cerebrovascular diseases are increasing in both rural and urban areas in recent fifty years. At present, cardiovascular and cerebrovascular diseases are the first cause of death due to diseases in China. Cardiovascular and cerebrovascular diseases are also the main cause of death in western countries.

Among all kinds of cardiovascular and cerebrovascular diseases, coronary heart disease is of particular concern. Coronary heart disease (CHD), the full name of which is coronary atherosclerotic heart disease, sometimes also known as ischemic heart disease or coronary disease, refers to the heart disease caused by myocardial ischemia and hypoxia due to coronary atherosclerosis. Coronary artery is the only blood vessel that supplies blood to the heart, and as its shape is like a crown, it is called coronary artery. This blood vessel will also become sclerotic along with the whole body blood vessels, showing an atherosclerotic change, causing cardiovascular blood circulation disorders and resulting in myocardial ischemia and hypoxia, namely coronary heart disease. CHD is a common and frequently occurring disease in middle-aged and elderly people, which seriously endangers people's lives. CHD can be divided into five types: occult type, angina pectoris, myocardial infarction, arrhythmia and sudden death.

Most cardiovascular diseases, including coronary heart disease, eventually lead to heart failure. Heart failure refers to the cardiac circulation disorder syndrome, the symptoms of which are mainly pulmonary congestion and vena cava congestion, wherein the venous return blood cannot be fully discharged from the heart due to systolic and/or diastolic dysfunction of the heart, resulting in blood stasis in the venous system and insufficient blood perfusion in the arterial system. Heart failure is usually not an independent disease, but the terminal stage of the development of some heart diseases. Clinically, heart failure can be manifested as acute heart failure and chronic heart failure. Etiologically, heart failure can be divided into systolic or diastolic heart failure For the treatment of coronary heart disease and heart failure, a lot of research has been done, but the outcome is not satisfactory. In particular, although there are some effective drugs for coronary heart disease and heart failure caused by cardiac systolic dysfunction (such as Entresto™), there has been no effective drug for coronary heart disease and chronic heart failure caused by myocardial diastolic dysfunction. However, coronary heart disease, heart failure and other cardiovascular diseases caused by myocardial diastolic dysfunction are very common in the middle-aged and elderly people. This is because with the increase of age, myocardial fibrosis is becoming more and more serious, and the range of myocardial diastolic movement is constantly shrinking, and the blood oxygen entering the myocardium will naturally decrease due to myocardial diastolic insufficiency, resulting in the clinical symptoms of myocardial ischemia and hypoxia. Because of myocardial diastolic insufficiency, the myocardial stroke becomes shorter, so the heart rhythm will be abnormal, probably leading to myocardial fibrosis. Diastolic dysfunction may also lead to blood stasis phenomenon, myocardial infarction, and sudden death.

Therefore, pharmaceuticals for the treatment of cardiovascular and cerebrovascular diseases (such as coronary heart disease, heart failure, etc.), especially those caused by myocardial diastolic dysfunction, are urgently needed.

Traditional Chinese Medicine (TCM) has been used in China for thousands of years. Generally, TCM is based on many chemical components in an herbal preparation that interact and act simultaneously through multiple molecular targets and cellular mechanisms. These multiple components serve various functions; some may be responsible for efficacy while others may decrease toxicity or increase bioavailability. Currently, mixtures of botanical extracts have been widely used throughout the world for the management of disease and they are widely recognized as having the advantages of less toxic side effects and better tolerance.

There are many reports about the treatment of coronary heart disease, heart failure and other cardiovascular or cerebrovascular diseases with traditional Chinese medicine. Coronary heart disease and heart failure are often diagnosed as chest obstruction in traditional Chinese medicine. According to the theory of traditional Chinese medicine, chest obstruction is a kind of disease characterized by chest tightness, chest pain (or even penetrating to the back) and shortness of breath. TCM diagnosis and treatment of chest obstruction can be divided into five types: heart blood stasis type, phlegm turbidity and blood stasis cold type, Yin cold stagnation type, heart and kidney Yin deficiency type, Qi and Yin deficiency type. "Lingshu•Five Evils" once pointed out: "evil in the heart, then heart aches." In addition, "Su Wen•Zang Qi Fa Shi Lun Pian" also said: "if there is a heart disease, the chest will be achy . . . "

Many traditional Chinese medicine compositions or preparations which are alleged to have therapeutic effects on cardiovascular or cerebrovascular diseases such as coronary heart disease and heart failure have been proposed in the prior art. However, these traditional Chinese medicine compositions are often complex (composed of more than ten or more kinds of medicinal materials), and most of them are simply tested with a small number of clinical patients only, and their efficacy has not been verified by strict and systematic in vitro and in vivo experiments that meet the requirements of modern pharmacology. In addition, due to the complex composition and unknown active ingredients of these prior art traditional Chinese medicine compositions, it is difficult to carry out strict quality control and standardization, and thus it is difficult to realize industrial production.

SUMMARY

An object of the present disclosure is to provide a novel Chinese medicine composition for the treatment and/or prevention of cardiovascular or cerebrovascular diseases (such as coronary heart disease, heart failure, angina pectoris, myocardial infarction, thrombosis, stroke, etc.).

Another object of the present disclosure is to provide a novel Chinese medicine combination for treating and/or preventing cardiovascular or cerebrovascular diseases caused by myocardial systolic dysfunction, myocardial diastolic dysfunction, thrombosis, myocardial ischemia, myocardial hypoxia, or myocardial fatigue, especially myocardial diastolic dysfunction.

In one aspect, the present disclosure provides a traditional Chinese medicine composition for the treatment of a cardiovascular or cerebrovascular disease, and the active ingredients thereof are composed of the following components 1) and 2):

1) an ethanol extract of 6-12 parts by weight of Rhizoma Chuanxiong and 5-10 parts by weight of Radix Curcumae; and 2) an aqueous extract of 5-10 parts by weight of Radix Cyathulae and the extraction residue of said ethanol extract of Rhizoma Chuanxiong and Radix Curcumae.

In the above traditional Chinese medicine composition, the extracts of Rhizoma Chuanxiong, Radix Curcumae and Radix Cyathulae are used as the active ingredients. It is understood by those skilled in the art that the traditional Chinese medicine composition can also comprise other auxiliary medicinal materials or excipients (such as auxiliaries, adjuvants or drug excipients, etc.) as required.

Therefore, in one embodiment, the traditional Chinese medicine composition may be consisting of the above component 1) and component 2). In other embodiments, the traditional Chinese medicine composition may further contain other auxiliary medicinal materials or excipients. For example, in another embodiment, a traditional Chinese medicine composition for the treatment of a cardiovascular or cerebrovascular disease is composed of the following components 1), 2) and 3):

1) an ethanol extract of 6-12 parts by weight of Rhizoma Chuanxiong and 5-10 parts by weight of Radix Curcumae;

2) an aqueous extract of 5-10 parts by weight of Radix Cyathulae and the extraction residue of said ethanol extract of Rhizoma Chuanxiong and Radix Curcumae; and 3) an aqueous extract of 5-10 parts by weight of Bulbus Allii Macrostemonis and 6-12 parts by weight of Cortex Eucommiae.

In another aspect, the present disclosure provides a method for preparing a traditional Chinese medicine composition, comprising the following steps:

(1) weighing 6-12 parts of Rhizoma Chuanxiong and 5-10 parts of Radix Curcumae, extracting them with ethanol and concentrating the extraction liquid;

(2) weighing 5-10 parts of Radix Cyathulae and mixing it with the extraction residue of step (1), extracting the mixture with water and concentrating the extraction liquid; and (3) combining the concentrates of step (1) and step (2) and then drying.

Furthermore, 5-10 parts of Bulbus Allii Macrostemonis and 6-12 parts of Cortex Eucommiae may be additionally added in the above step (2).

The traditional Chinese medicine composition disclosed herein can be formulated into various pharmaceutically acceptable oral dosage forms (such as tablets, capsules, granules, pills, oral liquid, etc.) as needed, which comprise the traditional Chinese medicine composition disclosed herein and a conventional medicinal adjuvant or auxiliary material.

The traditional Chinese medicine composition disclosed herein can also be formulated into various forms of oral health care products as needed, which comprise the traditional Chinese medicine composition disclosed herein and a conventional adjuvant or auxiliary material.

The traditional Chinese medicine composition disclosed herein can be used to treat or prevent cardiovascular or cerebrovascular diseases, especially coronary heart disease, heart failure (including systolic heart failure or diastolic heart failure), angina pectoris, myocardial infarction, thrombosis and stroke.

The traditional Chinese medicine composition disclosed herein is particularly suitable for treating and/or preventing myocardial systolic dysfunction, myocardial diastolic dysfunction, thrombosis, myocardial ischemia, myocardial hypoxia, or myocardial fatigue, or cardiovascular and cerebrovascular diseases caused by these diseases, especially myocardial diastolic dysfunction or cardiovascular and cerebrovascular diseases caused by myocardial diastolic dysfunction.

In another aspect, the present disclosure provides a method for treating or preventing a cardiovascular or cerebrovascular disease, in particular, such as coronary heart disease, heart failure (including systolic or diastolic heart failure), angina pectoris, myocardial infarction, thrombosis, and stroke, comprising administering a therapeutic effective amount of the Chinese medicine composition disclosed herein to a patient.

Due to the specific formula and/or extraction process adopted in the present disclosure, the medical composition as prepared may have at least one of the following advantages:

1. It has defined formulation and determined active ingredients, shows strong synergistic effect, and allows good stability and repeatability of its production process.

2. It has significant effects on myocardial systolic and diastolic dysfunction, platelet aggregation, thrombosis, myocardial ischemia, myocardial hypoxia, myocardial fatigue and so on, including the following aspects.

1) The treatment efficacy on heart failure caused by myocardial systolic dysfunction is comparable to the latest and best drugs in the world.

2) It has a significant treatment efficacy on chronic heart failure caused by myocardial diastolic dysfunction, which is superior to the latest and best drugs in the world.

3) It is significantly effective in treating myocardial ischemia and hypoxia.

4) It has significant antithrombotic effect and thrombolytic effect.

5) It has a significant effect on the recovery of damaged myocardium.

6) It can effectively improve myocardial fatigue.

3. It is safe and reliable (with excellent performance in both acute toxicity test and long-term toxicity test), is beneficial to liver and kidney function during the treatment of heart failure, and does not damage other organs of human body, indicating a better safety than similar drugs.

DETAILED DESCRIPTION

The disclosure provides a compound preparation, which is mainly used for the treatment of chest obstruction (diagnosed as coronary heart disease by modern medicine) and has been developed based on TCM theory about Qi stagnation and blood stasis combined with modern medical theory about myocardial systolic and diastolic dysfunction function.

According to the theory of traditional Chinese medicine, chest obstruction and heart pain are mainly caused by obstruction of heart Qi and blood circulation. According to modern medicine, coronary heart disease is mainly caused by imbalance between coronary blood flow and myocardial demand. They are highly consistent in this regard. According to the theory of traditional Chinese medicine, the etiology of chest obstruction is deficiency of vital energy in the body, invasion of external pathogenic factors, improper diet, excessive emotions, maladjustment of work and rest, etc., resulting in blockage of pulse and imbalance of Yin and Yang in the heart, Qi and blood. The disease is mainly manifested by suffocation and pain in the chest, and is considered to be equivalent to coronary heart disease or angina pectoris diagnosed by modern medicine.

The indications of the medical composition disclosed herein are chest obstruction and heartache, which are attributed to Qi stagnation and blood stasis and the symptoms of which are chest pain, chest tightness, palpitation, dark tongue or ecchymosis on tongue, and astringent or stringy pulse. The pathogenesis of chest obstruction and heartache is Qi stagnation and blood stasis. The disease is often caused by excessive emotions and abnormal emotions, which damage viscera, and the deficiency in viscera function leads to the loss of regulation of Qi and blood and in turn causes Qi stagnation and blood stasis, or caused by improper diet, such as overeating fat and sweet food, alcoholism and overeating raw and cold food, which causes injury to the spleen and stomach, promotes generation of phlegm and dampness-evil, and in turn leads to Qi stagnation and blood stasis due to the inhibition of Qi and blood circulation by dampness-evil; or caused by maladjustment of work and rest, wherein overwork consumes Qi and injures Yin, and excessive relaxation leads to stagnation of Qi and blood circulation, resulting in Qi stagnation and blood stasis. The obstruction of Qi and blood leads to chest tightness and heartache. "Ren Zhai Zhi Fang Lun" said: "Qi is the commander of blood, Qi flows then blood flows, Qi stops then blood stops, cold Qi leads to blood coagulation, and once the movement of Qi is interrupted the circulation of blood will be interrupted". Therefore, Qi stagnation leads to blood stasis, and blood stasis blocks heart pulse, causing chest tightness, chest pain, and shoulder and back pain. On the other hand, the formation of blood stasis can also block the movement of Qi, leading to Qi stagnation, because Qi is carried by blood, Qi arrives where blood arrives, Qi stops when blood stops, and Qi must be infused into the blood vessels so as to reach the whole body. So, Qi and blood are cause and effect for each other. Once the heart pulse is blocked, Qi and blood are blocked, and the heart will lose its nourishment, leading to palpitation. Qi stagnation and blood stasis can cause dark purple spots on the tongue and astringent and stringy pulse.

For the chest obstruction of Qi stagnation and blood stasis, the main treatment methods are promoting Qi movement and activating blood circulation, dredging meridians and collaterals, and relieving pain. In view of its main pathogenesis, the treatment should mainly aim at regulating the relationship between Qi and blood as well as the functional disorder and imbalance. Because "Qi flows then blood flows", the treatment of blood stasis should focus on regulation of Qi, and Qi moves smoothly when blood stasis is resolved. According to the "Theory of Blood Syndrome and Viscera Pathogenesis", "if Qi is flushed and regulated, the blood vessels will become smooth". If Qi and blood are regulated smoothly and blood vessels are unobstructed, the stasis disease will be eliminated. Therefore, promoting Qi movement, activating blood circulation and relieving pain are a kind of method for treating both root causes and symptoms.

The present disclosure provides a traditional Chinese medicine composition for the treatment of a cardiovascular or cerebrovascular disease, and the active ingredients are composed of the following components 1) and 2):

1) an ethanol extract of 6-12 parts by weight of Rhizoma Chuanxiong and 5-10 parts by weight of Radix Curcumae; and 2) an aqueous extract of 5-10 parts by weight of Radix Cyathulae and the extraction residue of said ethanol extract of Rhizoma Chuanxiong and Radix Curcumae.

The extracts of Rhizoma Chuanxiong, Radix Curcumae and Radix Cyathulae are used as the active ingredients of the traditional Chinese medicine composition. These three medicines can be used alone, or in combination with other auxiliary herbs, such as 5-10 parts of Bulbus Allii Macrostemonis and 6-12 parts of Cortex Eucommiae, which are used to assist in the treatment of complications caused by coronary heart disease and heart failure, such as shoulder and back pain.

Radix Curcumae (or Curcumae Radix): pungent, bitter, cool, acting on heart meridian, lung meridian and liver meridian. It can be used as a Monarch medicine and can cool blood and break blood stasis. According to the "*Compendium of Materia Medica*", it can "act on the heart and wrapping meridian" and can be used for "treating blood Qi and treating heart and abdominal pain".

Rhizoma Chuanxiong (also known as *Ligusticum wallichii*): pungent, warm, acting on liver, gallbladder and pericardial meridian. It can promote blood circulation and Qi movement. It can be used as a Minister medicine to relieve pain. The combination of the Monarch medicine and Minister medicine can strengthen the efficacy promoting blood circulation and Qi movement. Both of them act on the heart meridian or pericardium meridian, promote blood circulation and Qi movement, and provide benefits to the heart pulse.

Radix Cyathulae: sweet, slightly bitter, mild, acting on liver and kidney meridian. It is used as an Assistant medicine in the five-medicine formulation and as a Minister medicine in the three-medicine formulation to remove blood stasis and dredge collaterals. It can activate blood circulation and remove blood stasis, and has the function of dredging collaterals. According to the book of "Materia Medica Jing Shu", "it is beneficial to descending, . . . and it can expel Qi and blood, especially resolve Qi stagnation and blood coagulation".

Radix Curcumae can induce Qi in heart, lung and liver, Rhizoma Chuanxiong can guide Qi and blood to go up, and Radix Cyathulae can guide Qi and blood to go down. So, the combination of the three medicines (or five medicines) disclosed herein can make Qi and blood circulate around the body. Therefore, the movement of Qi and circulation of blood is promoted, blood stasis is removed, and pain is relieved. Radix Curcumae has slightly different pharmaceutical properties due to different places of production, wherein. *Curcuma* Wenyujin or Radix *Curcuma* Kwangsiensis are preferably used.

Bulbus Allii Macrostemonis (also known as *Allium macrostemon*): pungent, bitter and warm, acting on heart, lung, stomach and large intestine meridian. It can dredge Yang and disperse coagulation. It can be used as an Assistant medicine to help movement of Qi and remove stagnation. In the compositions, it helps the Monarch and Minister to dispel the chest obstruction, heartache and abdominal distension. According to "Ben Cao Qiu Zhen", it can "promote the flow of Qi, lubricate orifices, and help Yang".

Cortex Eucommiae (also known as *Eucommia ulmoides*): sweet, warm, acting on liver and kidney meridian and capable of tonifying liver and kidney. According to "Shennong Herbal Classic", it "mainly treats back pain". It can tonify liver and kidney, is beneficial to kidney Yang and heart Yang, and helps to keep the circulation of Qi and blood smooth. It is used to assist the Monarch and Minister to treat the pain of shoulder and back.

In the prior art, there are also some traditional Chinese medicine compositions alleged useful for treating coronary heart disease and other diseases, but the traditional Chinese medicine composition disclosed herein is different from any prior art composition. For example, Chinese patent application CN103933474A discloses a pharmaceutical composition for the treatment of coronary heart disease, which is a prepared from raw materials with the following weight ratios: 15-20 parts of *Salvia miltiorrhiza,* 10-15 parts of *Angelica sinensis,* 10-15 parts of unprocessed *Radix rehmanniae,* 10-15 parts of *Radix rehmanniae* preparata, 10-15 parts of *Paeoniae rubra,* 10-15 parts of *Semen persicae,* 7-11 parts of *Flos carthami,* 4-8 parts of Rhizoma Chuanxiong, 8-12 parts of *Cyperus rotundus,* 8-12 parts of Radix Curcumae, 8-12 parts of *Radix bupleuri,* 8-12 parts of Radix Paeoniae Alba, 4-8 parts of *Radix platycodonis,* 8-12 parts of Radix Cyathulae, and 4-8 parts of *Radix glycyrrhizae.* The medicine composition of CN103933474A also contains Rhizoma Chuanxiong, Radix Cyathulae and Radix Curcumae, but it is substantially different from the traditional Chinese medicine composition disclosed herein, as explained below.

From the perspective of traditional Chinese medicine, the composition of CN103933474A contains four kinds of Qi regulating and detoxifying medicines including *Cyperus rotundus, Radix bupleuri, Radix platycodonis* and *Radix glycyrrhizae,* five kinds of blood activating drugs including *Salvia miltiorrhiza, Semen persicae, Flos carthami,* Rhizoma Chuanxiong and Radix Cyathulae, and five blood tonic drugs including *Angelica sinensis,* unprocessed *Radix rehmanniae, Radix rehmanniae* preparata and *Paeoniae rubra,* and thus is used to replenish Qi and tonify blood, and its main indication is blood deficiency syndrome (mostly seen in middle-aged and elderly people). The composition disclosed herein is composed of Rhizoma Chuanxiong, Radix Cyathulae and Radix Curcumae (or further supplemented with Bulbus Allii Macrostemonis and Cortex Eucommiae), and its main indication is chest obstruction and heartache caused by Qi stagnation and blood stasis (mainly caused by excessive emotions or abnormal emotions, and seen in all age groups). Therefore, the two kinds of compositions are significantly different in formulation, pharmacology, efficacy and indication.

From the perspective of modern medicine or chemistry, as the composition of CN103933474A contains 15 herb medicines, the composition is very complex and the active ingredients are difficult to determine. Rhizoma Chuanxiong, Radix Cyathulae and Radix Curcumae account for a very small portion of the composition, and thus should not be considered as the main active ingredients of the composition. On the contrary, specific extracts of Rhizoma Chuanxiong, Radix Cyathulae and Radix Curcumae are used as the active ingredients of the composition disclosed herein. In addition, the composition of CN103933474A can be extracted with water or ethanol; while the traditional Chinese medicine composition disclosed herein cannot be obtained by simply mixing the raw materials and directly extracting them with water or ethanol, but can only be obtained by using a specific combination of extracts. Therefore, the active ingredients of the two compositions are obviously different at the molecular level.

Through a large number of in vivo and in vitro experiments using modern medical means, the inventor has demonstrated that the traditional Chinese medicine composition (including three-medicine formulation and the five-medicine formulation) has significant therapeutic effect on myocardial systolic and diastolic disorders, platelet aggregation and thrombosis, myocardial ischemia, hypoxia, myocardial fatigue, etc., and is safe and reliable, and has no toxic side effects on human body. Specifically, the following effects have been observed.

1) The treatment efficacy on heart failure caused by myocardial systolic dysfunction is comparable to the latest and best drugs in the world.

2) It has a significant treatment efficacy on chronic heart failure caused by myocardial diastolic dysfunction, which is superior to the latest and best drugs in the world.

3) It is significantly effective in treating myocardial ischemia and hypoxia.

4) It has significant antithrombotic effect and thrombolytic effect.

5) It has a significant effect on the recovery of damaged myocardium.

6) It can effectively improve myocardial fatigue.

The raw materials for the composition disclosed herein are all are commonly used herbs, and are described in detail in "Chinese Pharmacopoeia" and/or "Chinese Materia Medica", and can be easily obtained commercially.

In the context of the present disclosure, the term "ethanol" may refer to either absolute ethanol or an ethanol solution in water, for example 40-95% ethanol solution in water or 40-80% ethanol solution in water, preferably 50-70% ethanol solution in water. Depending on specific embodiments, ethanol aqueous solutions of various concentrations, such as 60%, 65%, 70%, etc., can be used. The above concentration refers to the volume concentration.

A herbal raw material or component referred to as "optional" in the present disclosure may be included in some embodiments while absent in other embodiments. Similarly, steps or processes referred to "optional" may be included in some embodiments while absent in other embodiments.

The amount of each medicine provided in the disclosure generally refers to its weight unless otherwise specified. It can be understood by those skilled in the art that a certain error is allowed for the amount specified herein, and the error is usually within the range of ±8%, ±5% or ±3%.

It has been found that the ratio of Radix Curcumae, Rhizoma Chuanxiong and Radix Cyathulae is very important, and the composition cannot show obvious efficacy when it is not within the ranges specified herein.

The preferred relative amount of each raw medicine used in the composition is as follows:

Rhizoma Chuanxiong: preferably 6-12 parts, more preferably 8-10 parts, and most preferably about 9 parts;

Radix Curcumae: preferably 5-10 parts, more preferably 6-8 parts, and most preferably about 7 parts;

Radix Cyathulae: Curcumae: preferably 5-10 parts, more preferably 6-8 parts, and most preferably about 7 parts.

When Bulbus Allii Macrostemonis and Cortex Eucommiae are used, the preferred relative amounts of them are as follows:

Bulbus Allii Macrostemonis: preferably 5-10 parts, more preferably 6-8 parts, and most preferably about 7 parts;

Cortex Eucommiae: preferably 6-12 parts, more preferably 8-10 parts, and most preferably about 9 parts.

It can be understood by those skilled in the art that any preferred dosage range of each raw herb medicine described above can be arbitrarily combined with any preferred dosage range of another raw herb medicine, and the various combinations thus obtained constitute specific embodiments within the scope of the disclosure. Therefore, the present disclosure provides some exemplary embodiments described below.

Surprisingly, the inventor has found that if Radix Curcumae, Rhizoma Chuanxiong and Radix Cyathulae are combined in the prescribed weight ratio and simply extracted by water or alcohol, the extract thus obtained could not or could hardly show the desirable pharmaceutical activity. Only by using the weight proportions and specific extract combinations specified in the present disclosure can the Chinese medicine composition with desirable pharmaceutical activity be obtained.

The traditional Chinese medicine composition for the treatment of cardiovascular or cerebrovascular diseases comprises active ingredients composed of the following components 1) and 2):

1) an ethanol extract of 6-12 parts by weight of Rhizoma Chuanxiong and 5-10 parts by weight of Radix Curcumae; and 2) an aqueous extract of 5-10 parts by weight of Radix Cyathulae and the extraction residue of said ethanol extract of Rhizoma Chuanxiong and Radix Curcumae.

The traditional Chinese medicine composition disclosed herein is preferably provided to patients in the form of processed premix or preparation for direct administration.

It should be noted that the component 1) in the composition, i.e. "an ethanol extract of 6-12 parts by weight of Rhizoma Chuanxiong and 5-10 parts by weight of Radix Curcumae", should not be interpreted as requiring Rhizoma Chuanxiong and Radix Curcumae to be extracted together at the same time. Instead, Rhizoma Chuanxiong and Radix Curcumae can be extracted by ethanol separately and then the extracts can be combined, and the combination of the two extracts is equivalent to component 1). Similarly, the component 2) in the composition, i.e. "an aqueous extract of 5-10 parts by weight of Radix Cyathulae and the extraction residue of said ethanol extract of Rhizoma Chuanxiong and Radix Curcumae", should not be interpreted as requiring Radix Cyathulae and the extraction residue of said ethanol extract of Rhizoma Chuanxiong and Radix Curcumae to be extracted together at the same time. Instead, Radix Cyathulae and the extraction residue of said ethanol extract of Rhizoma Chuanxiong and Radix Curcumae can be extracted by water separately and then the extracts can be combined, or Radix Cyathulae, the extraction residue of ethanol extract of Rhizoma Chuanxiong and the extraction residue of ethanol extract of Radix Curcumae can be extracted by water separately and then the extracts can be combined, and the combination of the these extracts is equivalent to component 2). The use of "component 1)" and "component 2)" in the present disclosure is only for convenience of expression, and does not mean to limit the number of components present in the traditional Chinese medicine composition disclosed herein. It can be understood by those skilled in the art that as long as a composition is substantially equivalent to the combination of the above component 1) and component 2), it falls within the scope of the traditional Chinese medicine composition disclosed herein.

Therefore, the traditional Chinese medicine composition disclosed herein is not limited by a specific preparation method. However, for the sake of cost and efficiency, the traditional Chinese medicine composition is preferably prepared by the following method. Specifically, the preparation method of the traditional Chinese medicine composition comprises the following steps:

(1) weighing 6-12 parts of Rhizoma Chuanxiong and 5-10 parts of Radix Curcumae, extracting them with ethanol and concentrating the extraction liquid;

(2) weighing 5-10 parts of Radix Cyathulae and mixing it with the extraction residue of step (1), extracting the mixture with water and concentrating the extraction liquid; and (3) combining the concentrates of step (1) and step (2) and then drying.

The operation parameters such as the duration of the extraction, the number of times of the extraction, the concentration of the ethanol solution, and the amount of the solvent for each step can be adjusted as needed.

In certain preferred embodiments, the process of step (1) is prepared as follows: weighing 6-12 parts (preferably 8-10 parts) of Rhizoma Chuanxiong and 5-10 parts (preferably 6-8 parts) of Radix Curcumae and combining them, extracting the combination thus obtained with 5×-10× (e.g. 8×) 50%-70% ethanol (e.g. 55%, 60% or 65% ethanol) for 1-3 times, 1-3 hours each time, filtering the obtained mixture, combining the extraction liquid(s) and concentrating the combined extraction liquid, preferably concentrating to a density of about 1.05-1.15 g/ml.

In certain preferred embodiments, the process of step (2) is prepared as follows: weighing 5-10 parts (preferably 6-8 parts) of Radix Cyathulae and mixing it with the extraction residue of step (1), extracting the mixture with 8×-15× (e.g. 8×-10×) with water under reflux for 1-3 times, 1-3 hours each time, filtering the obtained mixture, combining the extraction liquid(s) and concentrating the combined extraction liquid, preferably concentrating to a density of about 1.05-1.15 g/ml.

In certain preferred embodiments, the drying operation of step (3) may be carried out by any drying method commonly used in the pharmaceutical field, such as spray drying, microwave drying, vacuum drying, and the like, preferably by spray drying. If desirable, additives or carriers may be added in the drying process. Usually, a granular or powder solid composition is obtained after drying. The product may be subjected to optional post-processing.

The preparation method may comprise additional steps or operations, such as sterilization, heating, cooling or the like, before, after or during the above-mentioned step (1), step (2) and step (3).

In order to prepare the composition comprising the five raw medicines described herein, 5-10 parts of Bulbus Allii Macrostemonis and 6-12 parts of Cortex Eucommiae can be added in the above-mentioned step (2) so as to be extracted together with other medicinal materials; or an independent water extraction step for Bulbus Allii Macrostemonis and Cortex Eucommiae can be inserted between step (2) and step (3); or Bulbus Allii Macrostemonis can be added in step (2), and an independent water extraction step for Cortex Eucommiae can be inserted before step (3). Those skilled in the art can understand that the methods described above are equivalent and can be substituted for each other. Any description of one of the modes mentioned in the specification (including the claims) means that it can be replaced by an equivalent embodiment thereof.

It can be understood by those skilled in the art that, when necessary, the traditional Chinese medicine composition disclosed herein can be made into a preparation according to conventional techniques in pharmaceutical engineering using pharmaceutically acceptable carrier or adjuvant. The active pharmaceutical ingredient in the preparation may be from 0.1 to 99.9% (e.g., 1-99% or 50-98% or 50-95%, etc.), with the balance being a pharmaceutically acceptable carrier or adjuvant.

The preparation of the present disclosure can be in any pharmaceutically acceptable dosage form, including: granules, tablets, sugar-coated tablets, film-coated tablets, enteric coated tablets, capsules, oral liquids, dripping pills, dissolving granules, pills, pulvis, suspensions, powders or the like.

Preferably, the preparation of the present disclosure is an oral dosage form such as granules, tablets, capsules, pills or the like.

Preferably, the preparation of the present disclosure is in the form of a unit dosage form, in which a single unit of the formulation is for example a tablet, a pouch of granules, or a capsule.

The unit dosage form preferably comprises about 1% to about 90% (e.g., 20-80% or 30-60%) active pharmaceutical ingredient. For example, the unit dosage form for a single administration, such as a capsule, a tablet or a sugar-coated pill, may contain about 1 mg to about 100 g (e.g. 10 mg to 80 g, 50 mg to 50 g, 1 g to 20 g, etc.) active pharmaceutical ingredient.

To prepare a suitable dosage form, the traditional Chinese medicine composition of the present disclosure, as the active pharmaceutical ingredient, may be optionally mixed or combined with an inorganic or organic, solid or liquid pharmaceutically acceptable carrier or adjuvant suitable for administration. For example, suitable carriers include, in particular, fillers such as sugars (for example lactose), mannitol or sorbitol, cellulose preparations and/or calcium phosphate (tricalcium phosphate or calcium hydrogen phosphate); binders such as starch paste, gelatin, methyl cellulose and/or polyvinyl vinylpyrrolidone; disintegrants such as starch, carboxymethyl starch, crosslinked polyvinylpyrrolidone, agar, or alginic acid or a salt thereof (for example, sodium alginate).

In certain particular embodiments, the present disclosure further provides a method of treating a cardiovascular or cerebrovascular disease or condition in a patient in need thereof, the method comprises administering to the patient an effective amount of the traditional Chinese medicine composition according to any one of the embodiments disclosed herein. The patient is preferably a mammal, and more preferably a human being. The administration is preferably oral administration.

In certain particular embodiments, the present disclosure also provides use of the traditional Chinese medicine composition according to any one of the embodiments disclosed herein for treating a cardiovascular or cerebrovascular disease or condition. The patient is preferably a mammal, and more preferably a human.

In certain particular embodiments, the present disclosure also provides use of a traditional Chinese medicine composition according to any one of the embodiments disclosed herein for the manufacture of a medicament for the treatment of a cardiovascular or cerebrovascular disease or condition. The disease or condition is preferably a disease or condition in a mammal, especially a human. The medicament is preferably in oral form.

In certain particular embodiments, the present disclosure also provides a traditional Chinese medicine composition according to any one of the embodiments disclosed herein for use in the treatment of a cardiovascular or cerebrovascular disease or condition. The disease or condition is preferably a disease or condition in a mammal, especially a human. The Traditional Chinese medicine composition is preferably in oral form.

In some embodiments, the disclosure also provides an oral pharmaceutical preparation or health care product comprising a traditional Chinese medicine composition according to any embodiment and a conventional medicinal adjuvant or auxiliary material.

The terms "treat", "treating" and "treatment" used herein are to be construed to refer to prophylactic or preventive treatment, as well as curative or palliative treatment of a disease or condition.

In particular, the cardiovascular or cerebrovascular diseases suitable for treatment with the traditional Chinese medicine composition disclosed herein are coronary heart disease, heart failure (including systolic or diastolic heart failure), angina pectoris, myocardial infarction, thrombosis, stroke, etc.

The traditional Chinese medicine composition disclosed herein is suitable for treating and/or preventing myocardial systolic disorder, myocardial diastolic disorder, thrombosis, myocardial ischemia, myocardial hypoxia, or myocardial fatigue, or various cardiovascular and cerebrovascular diseases caused by these diseases, especially myocardial diastolic dysfunction or cardiovascular and cerebrovascular diseases caused by myocardial diastolic dysfunction.

In the present disclosure, the terms "diastolic heart failure" (DHF) and "heart failure with a normal ejection fraction" (HFNET) and "heart failure with preserved ejection fraction" (HFpEF) are considered to have the same meaning and can be used interchangeably.

In the present disclosure, the term "systolic heart failure" (SHF) and the term "heart failure with reduced ejection fraction" (HFrEF) are considered to have the same meaning and can be used interchangeably.

The mode and dosage of administration can be determined by a physician according to the specifics of the patient, especially the age, body weight, lifestyle, activity level, severity of disease, etc.

In general, a single dose for a mammal is in the range of about 1-20,000 mg/kg, e.g. 2-5,000 mg/kg. For example, for the preferred subject, i.e. a human being, a suitable dose may be in the range of 1-2,000 mg/kg, 2-1,000 mg/kg, 5-500 mg/kg or 10-400 mg/kg when administered as a herbal extract premix. If desired, such doses can be divided (optionally evenly) into several portions. The above mentioned doses may be administered at regular intervals, for example, three times a day, once a day, once a week, and the like.

The term "mg/kg" or "mg·kg$^{-1}$" used in the present disclosure means milligrams per kilogram of the body weight of the mammal (including human) to be treated, and "g/kg" or "g·kg$^{-1}$" means grams per kilogram of the body weight of the mammal (including human) to be treated. Other terms, like "mg/100 g" or "mg/10 g" should be interpreted similarly.

The preferred values and aspects in various embodiments mentioned above can be combined with each other arbitrarily, and various embodiments obtained by such combination are within the scope of the claims.

DRAWINGS

Figure 1A:
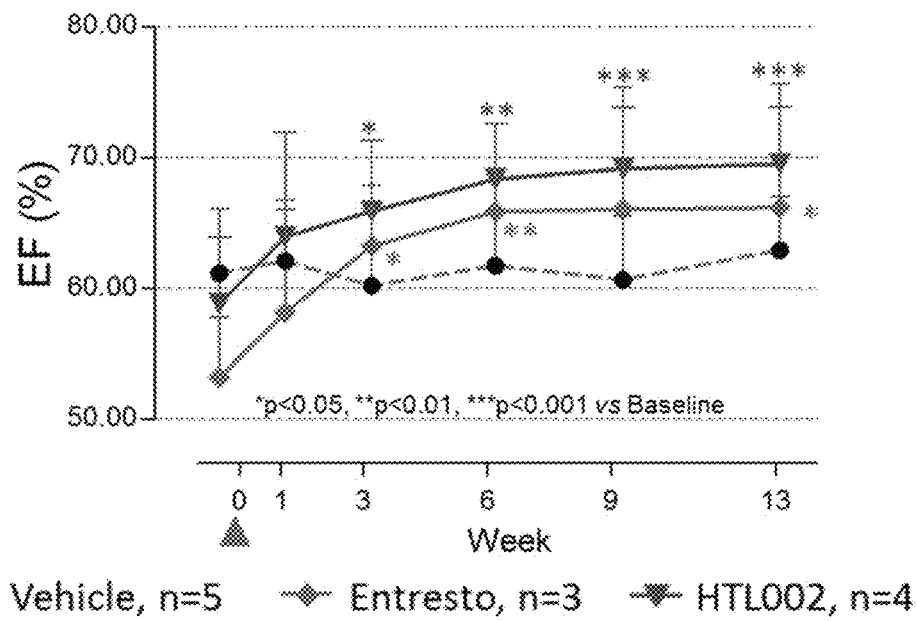
FIG. 1A illustrates the effects of different drugs on cardiac systolic function of rhesus monkeys after continuous administration with respect to the change trend of LVEF.
Figure 1B:
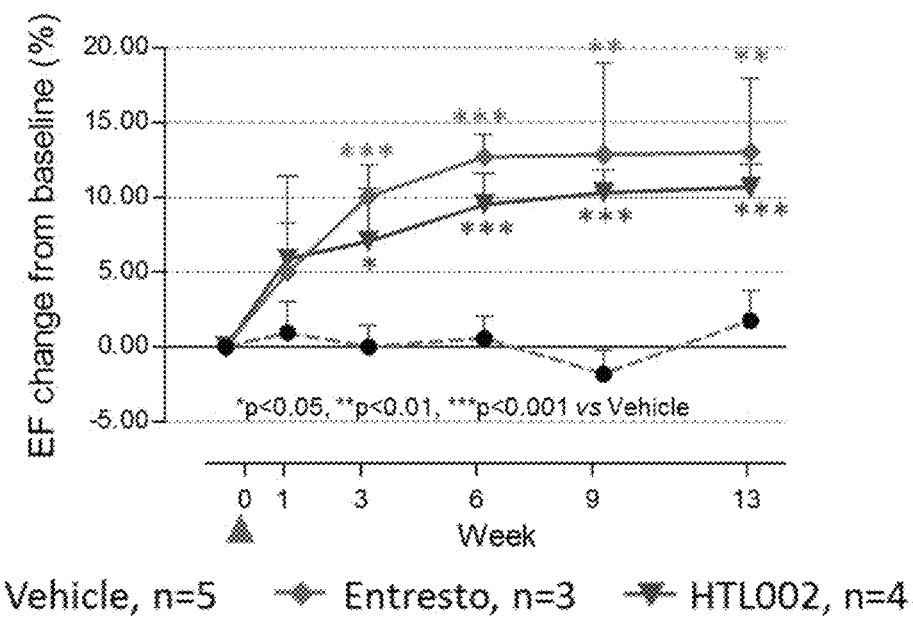
FIG. 1B illustrates the effects of different drugs on cardiac systolic function of rhesus monkeys after continuous administration with respect to the change trend of LVEF in each group relative to the baseline value.
Figure 1C:
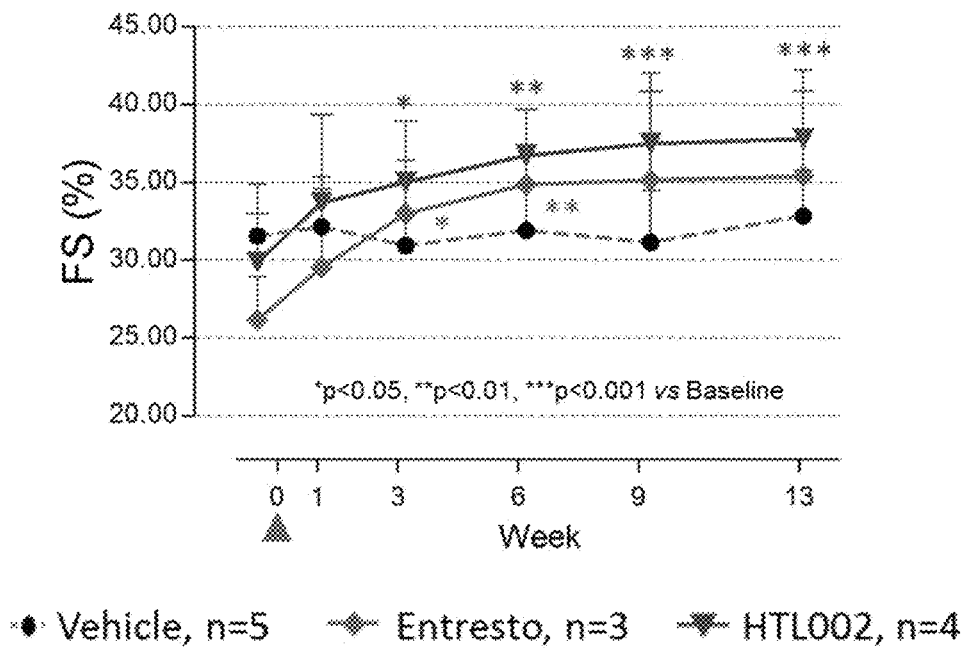
Figure 1D:
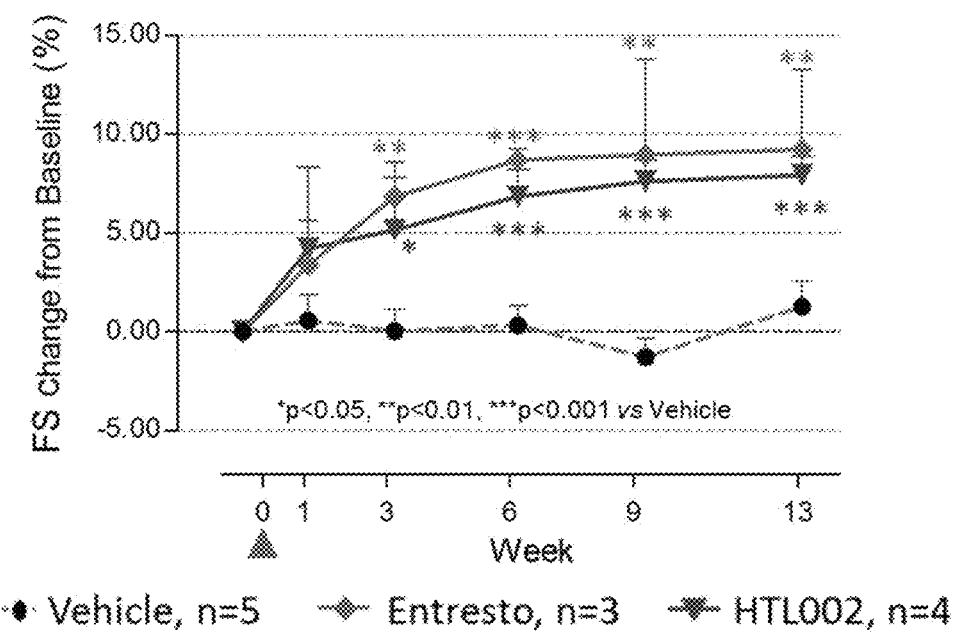

FIG. 1C illustrates the effects of different drugs on cardiac systolic function of rhesus monkeys after continuous administration with respect to the change trend of FS in each group; and FIG. 1D illustrates the effects of different drugs on cardiac systolic function of rhesus monkeys after continuous administration with respect to the change trend of FS in each group relative to the baseline value.

Figure 2A:
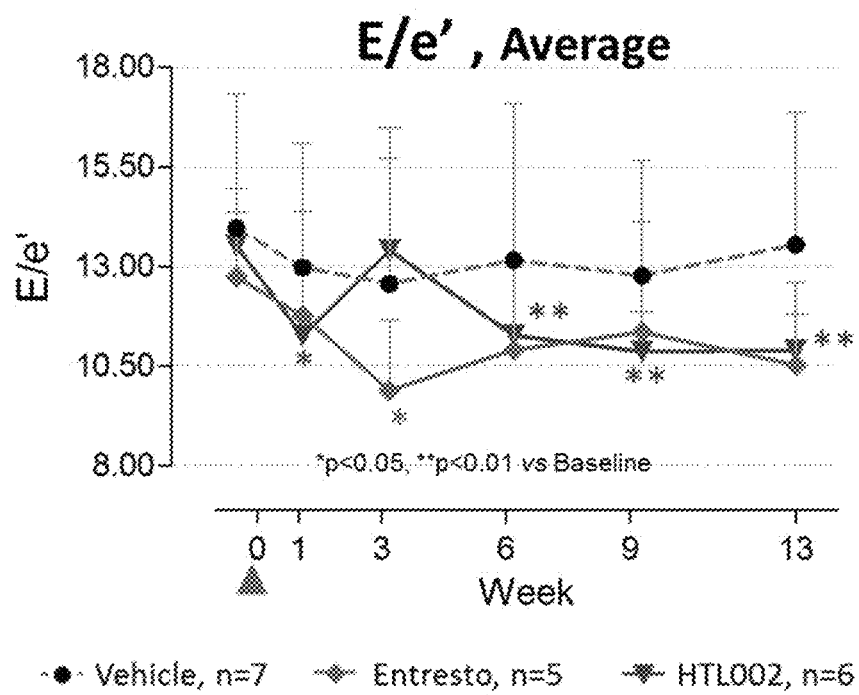
Figure 2B:
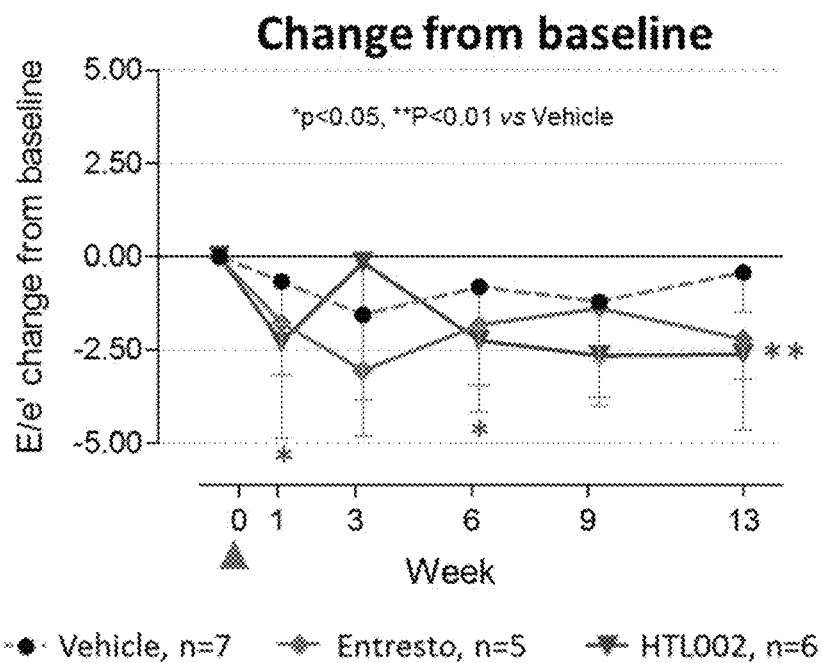
Figure 2C:
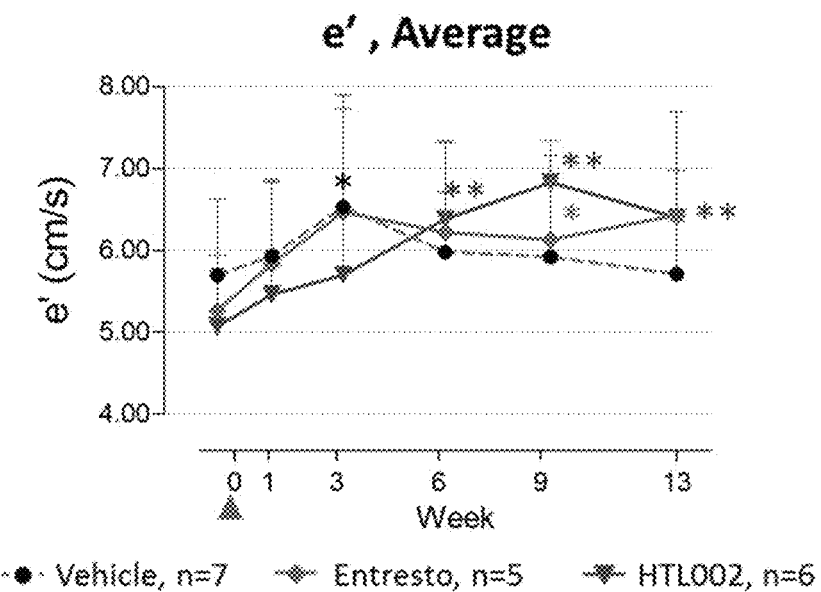
Figure 2D:
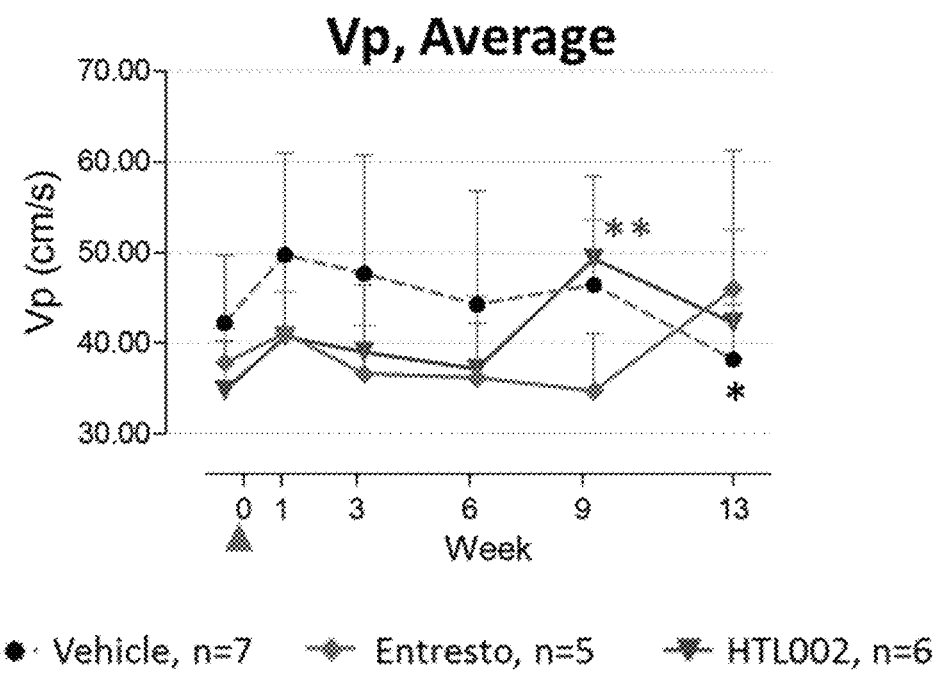

FIG. 2A illustrates the effects of different drugs on cardiac diastolic function of rhesus monkeys after continuous administration with respect to the change trend of;

FIG. 2B illustrates the effects of different drugs on cardiac diastolic function of rhesus monkeys after continuous administration with respect to the change trend of E/e' relative to the baseline value;

FIG. 2C illustrates the effects of different drugs on cardiac diastolic function of rhesus monkeys after continuous administration with respect to the change trend of e'; and FIG. 2D illustrates the effects of different drugs on cardiac diastolic function of rhesus monkeys after continuous administration with respect to the change trend of Vp.

EXAMPLES

The embodiments of the present invention will be further described in detail below by way of exemplary Examples. It is understood that the Examples described herein are merely illustrative and are not intended to limit the scope of the claims. Any modification made within the scope of the present disclosure, and any improvement made or equivalents obtained according to common technical knowledge and conventional means in the art should be included in the scope of the claims.

The numbers reported in the following Examples are as accurate as possible, but those skilled in the art will understand that each number should be understood as an approximate value rather than an absolutely accurate number due to unavoidable measurement errors and variation in operational parameters. For example, due to an error caused by weighing apparatus, the weight values for each material in each composition in the Examples should be understood as having a ±5% error.

Example 1: Preparation of Traditional Chinese Medicine Composition 1

The traditional Chinese medicine composition of Example 1 was composed of five raw medicines, i.e. Rhizoma Chuanxiong, Radix Curcumae, Radix Cyathulae, Bulbus Allii Macrostemonis and Cortex Eucommiae. Among the raw medicines as used, Rhizoma Chuanxiong was collected from Sichuan Province, China, Radix Curcumae was collected from Guizhou Province, China, Radix Cyathulae was collected from Sichuan Province, China, Bulbus Allii Macrostemonis was collected from Jiangsu Province, China, and Cortex Eucommiae was collected from Hebei Province, China.

The process for preparing the traditional Chinese medicine composition of Example 1 was as follows.

(1) 90 g Rhizoma Chuanxiong and 70 g Radix Curcumae were subjected to extraction with 8× 60% ethanol for 2.5h and the obtained mixture was filtered; and the filter residue was extracted with 8× 60% ethanol for another 2.5h, then the obtained mixture was filtered; and the filtrates obtained in these two extraction processes were combined and concentrated to a density of about 1.1 g/ml, affording a thick paste (the filter residue was reserved for future use);

(2) the filter residue obtained in the previous step was combined with 70 g Radix Cyathulae, 70 g Bulbus Allii Macrostemonis, and 90 g Cortex Eucommiae, the mixture thus obtained was subjected to extraction for 2 hours with 10× water and then filtered; then the filter residue was again subjected to extraction for 2 hours with 10× water and then filtered; the filtrates obtained in these two extraction processes were combined and concentrated to a density of about 1.1 g/ml, affording a thick paste; and (3) the thick paste obtained in step (1) and the thick paste obtained in step (2) were combined and spray dried to give the traditional Chinese medicine composition of Example 1 (referred to as "HTL001"). The resulting composition was a brown powder, and it was used directly in the following in vivo and in vitro experiments.

Example 2: Preparation of Traditional Chinese Medicine Composition 2

The traditional Chinese medicine composition of Example 2 was composed of three raw medicines, i.e. Rhizoma Chuanxiong, Radix Curcumae and Radix Cyathulae. Among the raw medicines as used, Rhizoma Chuanxiong was collected from Sichuan Province, China, Radix Curcumae was collected from Guizhou Province, China, and Radix Cyathulae was collected from Sichuan Province, China.

The process for preparing the traditional Chinese medicine composition of Example 2 was as follows.

(1) 90 g Rhizoma Chuanxiong and 70 g Radix Curcumae were subjected to extraction with 8× 65% ethanol for 2.5h and the obtained mixture was filtered; and the filter residue was extracted with 8× 65% ethanol for another 2.5h, then the obtained mixture was filtered; and the filtrates obtained in these two extraction processes were combined and concentrated to a density of about 1.1 g/ml, affording a thick paste (the filter residue was reserved for future use);

(2) the filter residue obtained in the previous step was combined with 70 g Radix Cyathulae, the mixture thus obtained was subjected to extraction for 2 hours with 8× water and then filtered; then the filter residue was again subjected to extraction for 2 hours with 8× water and then filtered; the filtrates obtained in these two extraction processes were combined and concentrated to a density of about 1.1 g/ml, affording a thick paste; and (3) the thick paste obtained in step (1) and the thick paste obtained in step (2) were combined and spray dried to give the traditional Chinese medicine composition of Example 2 (referred to as "HTL002"). The resulting composition was a brown powder, and it was used directly in the following in vivo and in vitro experiments.

Comparative Example 1: Preparation of Comparative Traditional Chinese Medicine Composition 1

90 g Rhizoma Chuanxiong, 70 g Radix Curcumae and 70 g Radix Cyathulae were subjected to extraction with 8× 65% ethanol for 2.5h and the obtained mixture was filtered; and the filter residue was extracted with 8× 65% ethanol for another 2.5h, then the obtained mixture was filtered; and the filtrates obtained in these two extraction processes were combined and concentrated to a density of about 1.1 g/ml, affording a thick paste, which was spray dried to give the traditional Chinese medicine composition of Comparative Example 1. The resulting composition was a brown powder.

Comparative Example 2: Preparation of Comparative Traditional Chinese Medicine Composition 2

90 g Rhizoma Chuanxiong, 70 g Radix Curcumae and 70 g Radix Cyathulae were subjected to extraction with 8× water for 2.5h and the obtained mixture was filtered; and the filter residue was extracted with 8× water for another 2.5h, then the obtained mixture was filtered; and the filtrates obtained in these two extraction processes were combined and concentrated to a density of about 1.1 g/ml, affording a thick paste, which was spray dried to give the traditional Chinese medicine composition of Comparative Example 2. The resulting composition was a brown powder.

The following are a variety of pharmacodynamic studies on the traditional Chinese medicine composition described in Example 1 or Example 2 as well as the traditional Chinese medicine composition of described in Comparative Example 1 or Comparative Example 2 to verify their efficacy.

1. Study on the Protective Effect of the Composition of Example 1 on Myocardial Ischemia Damage in SD Rats in Comparison to the Comparative Compositions In this study, a rat model of permanent myocardial ischemia was used to screen drugs against myocardial ischemia, and the effectiveness of the tested composition was determined.

1.1 Reagents and Instruments

Test substance: the composition of Example 2, the composition of Comparative Example 1 and the composition of Comparative Example 2 were dispersed/dissolved into distilled water to the specified concentration, respectively.

Positive control: Compound Danshen Dripping Pills, from Tianjin Tasly Pharmaceutical Co., Ltd., 27 mg/pill.

Triphenyltetrazolium chloride (TTC), from Sigma Company, was prepared into 1% solution with normal saline.

Pentobarbital sodium, from Sigma Company.

Sodium chloride injection, from Shandong Kelun Pharmaceutical Co., Ltd.

ALC-V8 animal ventilator, from Shanghai Alcott Biotechnology Co., Ltd.

C-5050ZOOM digital camera: from Olympus Company.

BIOPAC Systems MP150 electrocardiograph, from BIOPAC Company, USA.

1.2 Experimental Animals

SD rats, male, weighing 240-300 g, provided by China National Institute for Drug Control.

1.3 Experimental Methods

1) Animal Grouping and Treatment

After one week of adaptive feeding, the animals were randomly divided into Model control group, Compound Danshen Dripping Pills group (146 mg/kg, referred to as CDDP Group), Test group of the composition of Example 2 (270 mg/kg, referred to as Group 1), Comparative group of the composition of Comparative Example 1 (270 mg/kg, referred to as Group 2), and Comparative group of the composition of Comparative Example 2 (270 mg/kg, referred to as Group 3), with 6-7 rats in each group. The rats were fasted for 12 hours before the experiment.

2) Experimental Procedure

The animals were weighed and anesthetized by intraperitoneal injection of 3% pentobarbital sodium. After fixation, the rats were intubated and ventilated. ECG (electrocardiograph) recording needles (VIN+ for left lower limb, VIN− for right upper limb, and GND for left upper limb) were inserted to record ECG. The rats were subjected to thoracotomy at the left inferior axillary margin 3-4 intercostal or 4-5 intercostal and the pleura was torn. The left anterior descending branch of coronary artery was ligated with ⅜ 2×6 6/0 suture. The ECG changes were observed and the ischemic indications showed that the model was successful. Then the chest was closed by suturing. After 24 hours, the rats were weighed and anesthetized, and the heart was taken out and washed with normal saline, from which 4 pieces were cut and dyed with TTC for 6 minutes. The residual liquid was absorbed with filter paper, and the front and back sides of the pieces were photographed. Adobe Photoshop software was used to calculate the ratio of the infarct area to the left ventricular area.

1.4 Data Statistics

The data were expressed as Mean±SD and t-test was performed between groups.

1.5 Experimental Results

Compared with the model group (the ischemia area ratio of the model group was 24.3±3.5%), CDDP group (146 mg/kg) and Group 1 (270 mg/kg) after 7 days of continuous administration could significantly reduce the ratio of permanent myocardial ischemia infarct area in SD rats after 24 hours (see the table below).

TABLE 1

Influence of different compositions on the ratio of permanent myocardial ischemia infarct area in SD rats (n = 6-7)

| Groups | Dosage (mg/kg) | Ratio of infarct area (%) |
| --- | --- | --- |
| Model Group | — | 24.3 ± 3.5 |
| CDDP Group | 146 | 8.3 ± 3.4** |
| Group 1 | 270 | 6.0 ± 1.6** |
| Group 2 | 270 | 21.5 ± 4.1 |
| Group 3 | 270 | 22.3 ± 3.8 |

Compared with Model Group,
**$P < 0.01$ 1.6 Conclusion

The traditional Chinese medicine composition of Example 2 had protective effect on permanent myocardial ischemia in rats after continuous administration at the dose of 270 mg/kg for 7 days, while the compositions of Comparative Example 1 and Comparative Example 2 did not show obvious anti-myocardial ischemia effect although they were prepared from the raw medicines similar to the composition of Example 2. This result showed that a simple mixture of Rhizoma Chuanxiong, Radix Curcumae and Radix Cyathulae is not therapeutic, that is, the active pharmaceutical ingredients cannot be obtained by conventional alcohol extraction or water extraction. Surprisingly, the specific extraction method and extract combination of the present disclosure allow the composition as obtained have significant anti-myocardial ischemia effect.

2. Evaluation of Anti-Hypoxia Pharmacodynamics of the Traditional Chinese Medicine Composition of Example 2

In this study, the anti-fatigue and anti-hypoxia effects of the traditional Chinese medicine composition according to embodiments disclosed herein were evaluated in vivo by using anti-hypoxia models such as total oxygen consumption in sealed space under atmospheric pressure and load swimming model.

Experiment 1—Effect of the Traditional Chinese Medicine Composition of Example 2 on the Total Oxygen Consumption of Mice 1.1 Experimental Materials and Reagents Test substance: Chinese medicine composition of example 2 (HTL002), brown powder, dissolved in distilled water to the specified concentration.

Positive control: Compound Danshen Dripping Pills, produced by Tianjin Tasly Pharmaceutical Group Co., Ltd., 27 mg/pill, 10 pills a time, 3 times a day. The dosage of Compound Danshen Dropping Pills was calculated to be 105.3 mg/kg for mice by the body surface area method based on human dosage.

leads to deepening of respiration, enhancement of heart beat, increase of cardiac output and redistribution of blood to ensure blood supply to organs. In this experiment, the oxygen consumption in different time periods, death time (i.e. survival period) and oxygen consumption in survival period of mice were calculated under the condition of normobaric hypoxia.

The results showed that, as compared with the model group, the death time of animals in each dose group of the test substance was significantly prolonged ($P<0.05$); in term of oxygen consumption/20 g within 0-5 min, each dose group of the test substance was higher than the model group, among which the 300 mg/kg group was statistically different ($P<0.05$); in term of oxygen consumption/20 g within 5-10 min, each dose group of the test substance was significantly higher than the model group and the difference was statistically significant ($P<0.05$) (see table below).

TABLE 2

Influence of the Chinese medicine composition of Example 2 on the oxygen consumption in mice (n = 10)

| Groups | Dosage (mg/kg) | 0-5 min oxygen consumption/20 g | 5-10 min oxygen consumption/20 g | Oxygen consumption per unit time/20 g | Survival period (s) | Total oxygen consumption during survival |
|---|---|---|---|---|---|---|
| Model Group | — | 4.34 ± 0.53 | 2.00 ± 0.51 | 0.59 ± 0.07 | 697 ± 76 | 0.59 ± 0.07 |
| CDDP Group | 25 | 4.38 ± 1.18 | 2.59 ± 1.24 | 0.56 ± 0.13 | 869 ± 272 | 0.56 ± 0.13 |
|  | 50 | 4.49 ± 0.40 | 2.77 ± 0.52** | 0.62 ± 0.04 | 789 ± 90* | 0.62 ± 0.04 |
|  | 100 | 4.77 ± 0.27* | 2.43 ± 0.53 | 0.66 ± 0.04* | 733 ± 80 | 0.65 ± 0.04* |
|  | 200 | 4.77 ± 0.43 | 2.43 ± 0.48 | 0.65 ± 0.06* | 730 ± 87 | 0.65 ± 0.06* |
| HTL002 | 150 | 4.66 ± 0.48 | 2.82 ± 0.32** | 0.61 ± 0.06 | 836 ± 54** | 0.61 ± 0.06 |
|  | 300 | 5.04 ± 0.59* | 3.02 ± 0.46** | 0.64 ± 0.05 | 895 ± 107** | 0.64 ± 0.05 |
|  | 600 | 4.57 ± 0.59 | 2.58 ± 0.54* | 0.62 ± 0.10 | 797 ± 73** | 0.62 ± 0.10 |
|  | 1200 | 4.42 ± 0.45 | 2.68 ± 0.68* | 0.60 ± 0.07 | 862 ± 215* | 0.60 ± 0.07 |

Compared with Model Group,
**$P < 0.01$,
*$P < 0.05$

Sodium lime, Tianjin Fuchen Chemical Reagent Factory.

Experimental animals: ICR mice, male, 20-22 g, purchased from Peking University Medical Department (Experimental Animal Science Branch).

1.2 Experimental Methods

After one week of adaptive feeding, the animals were randomly divided into Model group (blank control group), Compound Danshen Dripping Pills groups (25 mg/kg, 50 mg/kg, 100 mg/kg and 200 mg/kg, referred to as CDDP Group), and Test substance groups (150 mg/kg, 300 mg/kg, 600 mg/kg and 1200 mg/kg), with 10 mice in each group. The mice were administered continuously for 15 days, once a day.

One hour after the last administration, the animals were put into a 250 ml sealed jar filled with 20 g sodium lime. The jar was sealed with a rubber stopper connected with a burette using silica gel, and the other end of the burette was inserted into water. The rising height of the liquid level in the burette at 0-5 min and 5-10 min, the time of animal death and the rising height of liquid level in the burette at the time of death were recorded respectively. After the experiment, the total oxygen consumption during survival period/20 g, oxygen consumption per unit time/20 g, 0-5 min oxygen consumption/20 g and 5-10 min oxygen consumption/20 g were calculated.

1.3 Data Statistics

The data were expressed as Mean±SD and t-test was performed between groups.

1.4 Experimental Results and Discussion

Due to incomplete oxidation of acid metabolites and accumulation of $CO_2$, normobaric hypoxia can stimulate chemoreceptors or central nervous system, which reflexively 1.5 Conclusion The traditional Chinese medicine composition of Example 2 had different degrees of anti-hypoxia effects on mice at dose of 150 mg/kg, 300 mg/kg, 600 mg/kg and 1200 mg/kg, respectively, for 15 days.

Experiment 2—Effect of the Traditional Chinese Medicine Composition of Example 2 on Swimming Time of Mice 1.1 Experimental Materials and Reagents Test substance: Chinese medicine composition of example 2 (HTL002), brown powder, dissolved in distilled water to the specified concentration.

Positive control: Compound Danshen Dripping Pills, produced by Tianjin Tasly Pharmaceutical Group Co., Ltd., 27 mg/pill, 10 pills a time, 3 times a day. The dosage of Compound Danshen Dropping Pills was calculated to be 105.3 mg/kg for mice by the body surface area method based on human dosage.

Experimental animals: ICR mice, male, 20-22 g, purchased from Peking University Medical Department (Experimental Animal Science Branch).

1.2 Experimental Methods

After one week of adaptive feeding, the animals were randomly divided into Model group (blank control group), Compound Danshen Dripping Pills groups (25 mg/kg, 50 mg/kg, 100 mg/kg and 200 mg/kg, referred to as CDDP Group), and Test substance groups (600 mg/kg and 1200 mg/kg), with 10 mice in each group. The mice were administered continuously for 15 days, once a day.

One hour after the last administration, the animals with iron wire of 9% body weight on the tail of each animal were put into a bucket with 20 cm depth of water at a temperature of 30° C. The mice were observed to swim to exhaustion (when the mice kept staying under water for 10 seconds and could not float up), and the time was recorded as the weight-bearing swimming time of mice.

1.3 Data Statistics

The data were expressed as Mean±SD and t-test was performed between groups.

1.4 Experimental Results and Discussion

Sports fatigue is caused by a series of biochemical changes of the body caused by the reduction of muscle contraction force. The most direct manifestation of sports fatigue is the decline of the body's sports endurance. In this experiment, the time of swimming with load can be used as an objective index to judge the physical strength and anti-fatigue ability of mice.

Compared with the model group, both the Compound Danshen Dripping Pills groups (50 mg/kg, 100 mg/kg, 200 mg/kg) and the test substance groups (600 mg/kg, 1200 mg/kg) showed significantly longer swimming time, with statistically significant difference (P<0.05) (see Table 2 below).

TABLE 3

Influence of the Chinese medicine composition of Example 2 on weight-bearing swimming time of mice (n = 10)

| Groups | Dose (mg/kg) | Swimming time (second) |
|---|---|---|
| Model Group | — | 70 ± 21 |
| CDDP | 25 | 88 ± 27 |
|  | 50 | 133 ± 52** |
|  | 100 | 161 ± 69** |
|  | 200 | 168 ± 121* |
| HTL002 | 600 | 113 ± 25** |
|  | 1200 | 144 ± 40** |

Compared with Model Group,
**P < 0.01,
*P < 0.05

1.5 Conclusion

The traditional Chinese medicine composition of Example 2 could significantly prolong the weight-bearing swimming time of mice and showed anti-fatigue effect at dose of 600 mg/kg and 1200 mg/kg, respectively, for 15 consecutive days.

The results of the above studies on the total oxygen consumption model in sealed space under atmospheric pressure and the weight-bearing swimming model showed that the Chinese medicine composition of Example 2 has anti-fatigue and anti-hypoxia effects to certain degrees on the test mice.

3. Effect of the Traditional Chinese Medicine Composition of Example 2 on Platelet Aggregation Platelet aggregation rate is a detection index of platelet function. The higher the platelet aggregation rate, the greater the possibility of thrombosis. In arteriosclerosis, coronary heart disease, cerebral infarction, hypertension, diabetes and other thrombotic diseases, platelet aggregation rate is often increased. When the platelet aggregation rate decreases upon treatment, it can not only inhibit thrombosis, but also dissolve the formed thrombus. Therefore, the determination of platelet aggregation rate can be used to observe the curative effect and screen drugs. In this study, thrombin induced rat platelet aggregation model was used to evaluate the inhibitory effect of the traditional Chinese medicine composition on platelet aggregation.

Thrombin induced rat platelet aggregation model is a classic model. Thrombin is a serine protease, which is also the main effector protease in the blood coagulation cascade reaction. Thrombin is produced by non-active prothrombin in prothrombin complex through protein cleavage under the action of factor Xa (FXa).

1.1 Experimental Materials and Reagents

Test substance: Chinese medicine composition of Example 2 (HTL002), brown powder, dissolved in distilled water to the specified concentration.

Positive control drug: Plavix (Clopidogrel Hydrogen Sulphate Tablets), from Sanofi (Hangzhou) Pharmaceutical Co., Ltd., 75 mg/tablet, once a day and one tablet per time. The dosage of Plavix was calculated to be 6.75 mg/kg for rats by the body surface area method based on human dosage.

Thrombin, from Sigma Company.

Pentobarbital sodium, from Sigma Company.

Instruments:

Platelet aggregation analyzer, model: LBY-NJ4, from Beijing Precil Instrument Co., Ltd.

Disposable human venous blood sample collection container, from Liuyang Medical Instrument Factory, Hunan Province.

Needle for disposable vacuum blood collector, from Shanghai Kangnong Medical Equipment Co., Ltd.

Low speed centrifuge, model: LD5-2A, Beijing Jingli Centrifuge Co., Ltd.

Experimental Animals:

SD rats, male, weighing 240-260 g, were provided by Experimental Animal Center, Academy of Military Medical Sciences, PLA.

1.2 Experimental Methods

1) Grouping of Animals and Administration Methods

After 5 days of adaptive feeding, the animals were randomly divided into blank control group, positive control group (Plavix group, 6.75 mg/kg) group and test substance group (800 mg/kg), with 20 rats in each group. The animals were administered by gavage for 15 consecutive days, once a day.

2) The Operation Steps were as Follows:

After the last administration, 3% Pentobarbital Sodium was injected intraperitoneally for anesthesia (40 mg/kg). 6 ml blood was collected from abdominal aorta into a disposable human venous blood sample collection container, which was reversed and shaken to mix the sample well. After 10 minutes of centrifugation at 800 rpm, the upper platelet rich plasma (PRP) was aspirated and the number of platelets was counted. The blood having the platelet rich plasma (PRP) removed was centrifuged at 3000 rpm for 10 minutes to obtain the platelet poor plasma (PPP).

A small magnetic rod and 300 μl PRP were added into a square cup, which was preheated for 5 minutes in a constant temperature hole, and 300 μl PPP was added into another square cup. 5 μl thrombin (5 U/L) was aspirated with a micro sampler and added to the bottom of each cup. The maximum platelet aggregation rate was measured, wherein 3-4 parallel tests were performed for each blood sample and the average value was taken.

1.3 Data Statistics

The data were expressed as Mean±SD and t-test was performed between groups.

1.4 Experimental Results and Discussion

In this experiment, the maximum platelet aggregation rate (35.8±29.7%) in the positive control drug Plavix group (6.75 mg/kg) was significantly lower than that in the model group (65.0±16.6%) (P<0.01), indicating the model was successful.

At the dose of 800 mg/kg, the test substance group showed a maximum platelet aggregation rate (40.8±23.5%)

which was significantly lower than that of the model group, and the difference was statistically significant (P<0.01), suggesting that the test substance had the effect of inhibiting platelet aggregation at the dose of 800 mg/kg (see the table below).

TABLE 4

Effect of the traditional Chinese medicine composition on thrombin induced platelet aggregation in rats

| Groups | Dose (mg/kg) | Maximum platelet aggregation rate (%) |
| --- | --- | --- |
| Model Group | — | 65.0 ± 16.6 |
| Plavix | 6.75 | 35.8 ± 29.7** |
| HTL002 | 800 | 40.8 ± 23.5** |

Compared with Model Group,
**P < 0.01,
*P < 0.05

1.5 Conclusion

The test substance (HTL002) could inhibit platelet aggregation upon administration at the dose of 800 mg/kg by gavage for 15 consecutive days.

4. Effect of the Traditional Chinese Medicine Composition on Arteriovenous Bypass Thrombosis in Rats 1.1 Experimental Materials and Reagents Test substance: Chinese medicine composition of Example 2 (HTL002), brown powder, dissolved in distilled water to the specified concentration.

Positive control drug: Plavix (Clopidogrel Hydrogen Sulphate Tablets), from Sanofi (Hangzhou) Pharmaceutical Co., Ltd., 75 mg/tablet, once a day and one tablet per time. The dosage of Plavix was calculated to be 6.75 mg/kg for rats by the body surface area method based on human dosage.

Instruments:

Electronic balance, model: FA1004, from Shanghai Yueping Scientific Instrument Co., Ltd.

Medical suture (5M sterilized coil), model: 0, from Shanghai Pudong Jinhuan Medical Supplies Co., Ltd.

Experimental Animals:

SD rats, male, weighing 240-260 g, were provided by Peking University Medical Department (Experimental Animal Science Branch).

1.2 Experimental Methods

1) Grouping of Animals and Administration Methods

After 5 days of adaptive feeding, the animals were randomly divided into blank control group, positive control group (Plavix group, 6.75 mg/kg), and four test substance groups (100, 200, 400 and 800 mg/kg), with 20 rats in each group. The animals were administered by gavage for 15 consecutive days, once a day.

2) The Operation Steps were as Follows:

After the last administration, 3% Pentobarbital Sodium was injected intraperitoneally for anesthesia (40 mg/kg). The right common carotid artery and left external jugular vein were separated. A 6 cm long medical surgical suture (No. 0) was placed in the middle of a polyethylene tube, which was filled with normal saline and inserted into the right common carotid artery and the left external jugular vein respectively to form an arteriovenous vascular loop. After 15 minutes, the blood flow was cut off, and the suture was taken out and weighed.

1.3 Data Statistics

The data were expressed as Mean±SD and t-test was performed between groups.

1.4 Experimental Results and Discussion

In this experiment, the classical rat arteriovenous bypass was used to form the bypass arteriovenous blood flow. When the platelets in the arterial blood flow contact the rough surface of the suture, they adhere to the suture, and the platelet aggregation forms platelet thrombosis around the surface of the suture. When platelet adhesion and aggregation function is inhibited, the weight of thrombosis become smaller. Therefore, the adhesion and aggregation function of platelets can be measured by thrombus weight.

In this experiment, the net weight of suture (20.2±4.8 mg) in the positive control group (6.75 mg/kg) was significantly reduced compared with that in the blank control group (59.1±14.2 mg), and the difference was statistically significant (P<0.01), indicating the model was successful.

The experimental results are shown in the table below. At the dose of 800 mg/kg, the net weight of thrombus in the test substance group (47.8±17.2 mg) was lower than that of the blank control group, and the difference was statistically significant (P<0.05), indicating that the test substance had the effect of inhibiting thrombosis at the dose of 800 mg/kg. At the doses of 100, 200 and 400 mg/kg, the net weight of suture was similar to that of the blank control group, but there was no statistical significance (P>0.05).

TABLE 5

Effect of the traditional Chinese medicine composition on arteriovenous bypass thrombosis in rats (Mean ± SD)

| Groups | Dose (mg/kg) | Net weight of suture (mg) |
| --- | --- | --- |
| Model Group | — | 59.1 ± 14.2 |
| Plavix | 6.75 | 20.2 ± 4.8** |
| HTL002 | 200 | 57.8 ± 14.6 |
|  | 400 | 63.0 ± 17.7 |
|  | 800 | 47.8 ± 17.2* |

As compared with the blank control group,
*P < 0.05,
**P < 0.01

1.5 Conclusion

The test substance could inhibit the formation of arteriovenous bypass thrombosis upon administration at the dose of 800 mg/kg by gavage for 15 consecutive days.

5. Pharmacodynamic Study on Rhesus Monkeys with Spontaneous Chronic Heart Failure after 3 Consecutive Months of Oral Administration Heart failure is one of the leading causes of death in the world. Entresto™ is a double acting angiotensin II receptor-neprilysin inhibitor developed by Novartis, which was approved by FDA in 2015. It is well recognized as the first-line drug and the best choice for clinical treatment of heart failure. Clinical data show that Entresto™ is very effective in the treatment of heart failure with low ejection fraction (HFrEF); however, the efficacy of Entresto™ on heart failure with preserved ejection fraction (HFpEF), which accounts for about half of patients with heart failure, has not been supported by clinical data. HFpEF is a disease with high incidence rate and high mortality rate, but there has been no effective therapy.

Spontaneous rhesus monkey chronic heart failure model is the world's best clinical model, which is highly similar to human in etiology, pathogenesis, disease progression and other aspects. Therefore, it is the best animal model for studying the pathogenesis of human heart failure, developing early diagnosis and treatment methods, screening and evaluation of new anti-heart failure drugs. This study will evaluate the pharmacodynamics and safety of the composition of Example 2 and Entresto™ on the systolic and diastolic functions in rhesus monkeys with spontaneous heart failure, and evaluate the efficacy at different doses. The experimental scheme and specific experimental procedure were designed with reference to the following references (and references cited therein):

Reference 1: Nagueh, Sherif F., et al. "Recommendations for the evaluation of left ventricular diastolic function by echocardiography." Journal of the American Society of Echocardiography 22.2 (2009): 107-133.

Reference 2: Solomon, Scott D., et al. "The angiotensin receptor neprilysin inhibitor LCZ696 in heart failure with preserved ejection fraction: a phase 2 double-blind randomised controlled trial." The Lancet 380.9851 (2012): 1387-1395.

Reference 3: Hansen, B. C., and N. L. Bodkin. "Heterogeneity of insulin responses: phases leading to type 2 (non-insulin-dependent) diabetes mellitus in the rhesus monkey." Diabetologia 29.10 (1986): 713-719.

Reference 4: Qian, Can, et al. "Diastolic dysfunction in spontaneous type 2 diabetes rhesus monkeys: a study using echocardiography and magnetic resonance imaging." BMC cardiovascular disorders 15.1 (2015): 59.

Reference 5: Jeong, Euy-Myoung, et al. "Role of mitochondrial oxidative stress in glucose tolerance, insulin resistance, and cardiac diastolic dysfunction." Journal of the American Heart Association 5.5 (2016): e003046.

1.1 Experimental Animals

104 Male rhesus monkeys (aged from 10 to 21 years) were provided by Ya'an Primed Shines Biotechnology Co., Ltd. (Sichuan Province, China) for diagnosis and evaluation of cardiac function by means of MRI and ECG. The following parameters were measured and calculated by conventional methods (such as those described in above Reference 1, Reference 2 and references cited therein)

LVEF: Left Ventricular Ejection Fraction;
FS: Fraction Shortening;
EDV: End Diastolic Volume;
ESV: End Systolic Volume;
SV: Stroke Volume;
E: Peak velocity of mitral blood flow in early diastolic phase;
e': Peak velocity of mitral annulus motion in early diastolic phase;
a': Peak velocity of mitral annulus motion in late diastolic phase;
S: Peak velocity of pulmonary venous flow in systolic phase;
D: Peak velocity of pulmonary venous flow in early diastolic phase;
Ar: Peak velocity of pulmonary venous flow reversal in late diastolic phase;
Ar-Adur: Difference between the duration of pulmonary venous flow reversal and that of mitral blood flow in late diastolic phase;
Vp: Left ventricular flow propagation velocity (velocity of propagation);
SBP: Systolic blood pressure;
DBP: Diastolic blood pressure.

Data analysis was completed by EchoPAC Software.

Then, according to the human diagnostic criteria, the rhesus monkeys were classified based on the measured parameters, Patients with LVEF<65% and FS<35% were diagnosed as systolic dysfunction (SD);

Patients with e'<8 and E/e'>10 were diagnosed as diastolic dysfunction (DD).

Finally, in consideration of the general health status of animals, 12 SD monkeys and 18 DD monkeys were selected for the experiment.

The animals were fed with 18% fat diet.

1.2 Experimental Methods

1) Animal Grouping

SD monkeys were randomly divided into three groups: test group (n=4), positive control group (Entresto group, n=3) and placebo group (n=5).

DD monkeys were randomly divided into three groups: test group (n=6), positive control group (Entresto group, n=5) and placebo group (n=7).

2) Experimental Design and Administration Scheme

The quarantine and preparation period was 4 weeks, and the animals were administered by gavage for 13 weeks. The specific doses were as follows:

Entresto group (administration of Entresto): 1.66 mg/kg in the first 2 weeks; 3.32 mg/kg in the second 2 weeks; 6.64 mg/kg in the third 2 weeks; and 13.33 mg/kg in the last 7 weeks.

Test group (administration of HTL002): 130 mg/kg in the first 2 weeks, 200 mg/kg in the following 4 weeks, and 250 mg/kg in the last 7 weeks.

Placebo group: administration of drug solvent.

3) Observation Index

During the experiment, the animals were observed once a day in cages for skin, hair, eyes, ears, nose, mouth, chest, abdomen, genitourinary department, limbs and other parts, as well as respiratory, exercise, urinary, defecation and behavior changes.

The baseline values of LVEF, FS, EDV, ESV, SV, E, e', a', S, D, Ar, Ar-ADur, Vp, SBP, DBP, and glomerular filtration rate (GFR) were measured and recorded before administration. The above parameters were measured again at the end of 1, 3, 6, 9 and 13 weeks during administration.

1.3 Data Statistics

The data were expressed as Mean±SD and t-test was performed between groups.

1.4 Experimental Results and Discussion

1) Baseline Values Before Administration

The values of various parameters determined before administration are shown in the table below.

TABLE 6

Base line values of rhesus monkeys having spontaneous systolic dysfunction or diastolic dysfunction

| | | Systolic dysfunction | | | Diastolic dysfunction | | |
|---|---|---|---|---|---|---|---|
| Items | Normal Range | Placebo (n = 5) | Entresto (n = 3) | HTL002 (n = 4) | Placebo (n = 7) | Entresto (n = 5) | HTL002 (n = 6) |
| Age (years) | / | 13 ± 1 | 16 ± 2* | 11 ± 3 | 14 ± 2 | 16 ± 2* | 14 ± 4 |
| Diabetes phase | Phase 1-2 | Phase 4-5 | Phase 4-6 | Phase 3-5 | Phase 5-7 | Phase 4-6 | Phase 3-5 |
| LVEF (%) | 75.21 ± 1.97 | 61.15 ± 4.95 | 53.17 ± 4.63 | 58.83 ± 5.13 | 68.72 ± 5.27 | 60.87 ± 11.41 | 6.98 ± 10.84 |
| FS (%) | 42.24 ± 1.80 | 31.56 ± 3.36 | 26.16 ± 2.81 | 29.87 ± 3.16 | 37.10 ± 4.28 | 31.76 ± 8.24 | 36.44 ± 8.74 |
| E/e' | 8.05 ± 0.97 | 10.48 ± 3.25 | 14.05 ± 1.45 | 12.03 ± 2.85 | 13.97 ± 3.36 | 12.74 ± 2.23 | 13.52 ± 0.77 |

TABLE 6-continued

Base line values of rhesus monkeys having spontaneous systolic dysfunction or diastolic dysfunction

| | | Systolic dysfunction | | | Diastolic dysfunction | | |
|---|---|---|---|---|---|---|---|
| Items | Normal Range | Placebo (n = 5) | Entresto (n = 3) | HTL002 (n = 4) | Placebo (n = 7) | Entresto (n = 5) | HTL002 (n = 6) |
| e' (cm/s) | 9.56 ± 1.31 | 6.79 ± 1.61 | 4.98 ± 0.40 | 6.30 ± 2.79 | 5.70 ± 0.93 | 5.27 ± 0.51 | 5.07 ± 0.79 |
| Ar-ADur (ms) | 40.09 ± 17.06 | −15.06 ± 20.59 | −12.50 ± 11.04 | −18.31 ± 19.60 | −13.09 ± 19.75 | −4.83 ± 15.23 | 18.04 ± 12.90 |
| Vp (cm/s) | 65.24 ± 8.44 | 49.37 ± 9.55 | 36.96 ± 1.61 | 38.19 ± 16.70 | 42.23 ± 7.47 | 37.83 ± 2.46 | 34.78 ± 6.23 |
| SBP (mmHg) | 119 ± 12 | 124 ± 10 | 127 ± 4 | 125 ± 3 | 127 ± 7 | 128 ± 5 | 130 ± 7 |
| DBP (mmHg) | 58 ± 7 | 61 ± 7 | 64 ± 3 | 59 ± 1 | 63 ± 5 | 63 ± 3 | 61 ± 3 |
| Glomerular filtration rate (ml/min/1.73 m$^2$) | >90 | 58.99 ± 11.04 | 75.44 ± 7.21 | 71.09 ± 9.23 | 64.11 ± 12.37 | 73.46 ± 6.79 | 71.49 ± 11.79 |

2) Change of Parameters after Administration

The experimental results are shown in FIGS. 1 to 2. In each figure, "week" means the week after the start of administration, "vehicle" refers to placebo group, "HTL002" refers to test substance group, "Entresto" refers to positive control group, and "baseline" refers to the baseline values.

FIG. 1 shows the effects of different drugs on cardiac systolic function of rhesus monkeys after continuous administration, where (a) is the change trend of LVEF, (b) is the change trend of LVEF in each group relative to the baseline value, (c) is the change trend of FS in each group, and (D) is the change trend of FS in each group relative to the baseline value.

It can be seen from FIG. 1 that LVEF and FS were improved 1 week after administration of HTL002 and Entresto, and maintained significant enhancement during 3-13 weeks of administration; while there was no significant change in placebo group before and after administration. It can be concluded from FIG. 1 that the systolic function of rhesus monkey can be significantly enhanced after treatment with Entresto or HTL002 for 13 weeks.

FIG. 2 shows the effect of different drugs on cardiac diastolic function of rhesus monkeys after continuous administration, where (a) is the change trend of E/e', (b) is the change trend of E/e' relative to the baseline value, (c) is the change trend of e', and (D) is the change trend of Vp.

It can be seen from FIG. 2 that HTL002 significantly improved the diastolic function of rhesus monkeys with spontaneous diastolic dysfunction after 9-13 weeks of treatment, while Entresto did not significantly improve the diastolic function after 13 weeks of treatment.

In addition, no side effects were observed in HTL002 group and Entresto group during the whole treatment period.

1.5 Conclusion

According to the above experimental results, it can be concluded that:

HTL002 and Entresto both can significantly improve the systolic function during 3-13 weeks of treatment, suggesting that HTL002 can be used in the treatment of patients with chronic heart failure with low ejection fraction, and the onset time and efficacy are similar to that of Entresto.

Compared with the baseline, the diastolic function was significantly improved during 9-13 weeks of HTL002 treatment, while the diastolic function was not significantly improved after 13 weeks of Entresto treatment, suggesting that HTL002 can improve the diastolic function in patients with chronic heart failure with preserved ejection fraction, but the related mechanism needs to be further investigated.

HTL002 is safe and has no side effects on rhesus monkeys after 3 months of administration.

6. Acute Toxicity Test of the Composition of Example 2

1.1 Experimental Animals

40 ICR mice, half male and half female, aged 28-35 days, provided by Beijing Charles River Experimental Animal Technology Co., Ltd. were used, wherein the body weight of female mice was 15.2-17.5 g, and that of male mice was 15.5-18.3 g.

1.2 Experimental Procedure

The feeding conditions were as follows: room temperature 22.2±1.2° C., relative humidity 46.9±4.0%, minimum ventilation rate 15 times/h, light illumination: dark=12h: 12 h. The animals were raised in a PC mouse group rearing box, with cage size of 294*190*125 mm$^3$ and 5 mice in each box. The animals were allowed to eat and move freely during the whole feeding process. The adaptation period was 6 days.

Grouping Methods: the animals were weighed before the experiment, and the male and female animals were randomly divided into two groups—administration group (HTL002) and solvent control group, with 20 mice in each group, half male and half female. The experimental animals were fasted for about 4 hours before and 1-2 hours after administration, but were allowed to drink freely. The specific administration scheme is shown in the table below.

TABLE 7

Test dose and grouping of ICR mice for single dose toxicity test

| | Dose | Concentration | Number of animals | |
|---|---|---|---|---|
| Groups | (g · kg$^{-1}$) | (mg · ml$^{-1}$) | ♀ | ♂ |
| I | 0 | 0 | 10 | 10 |
| II | 32 | 800 | 10 | 10 |

Administration scheme: the maximum dosage method was used in this experiment. 0.5% CMC Na solution provided by China Pharmaceutical Group Chemical Reagent Co., Ltd. was used as the solvent. The concentration of the substance was 0.8 g/ml, and the single dose volume for intragastric administration was 0.4 ml/10 g, totally once. In other words, the dose of the test substance for single gavage was 32 g/kg, which was about 500 times of the proposed human clinical dose.

The reaction of the animals to the test substance was observed within 4 hours after the administration, and then observed once a day for 14 consecutive days.

1.3 Experimental Results:

In the solvent control group, no obvious abnormality was observed for 4 hours and 14 days after administration. No obvious abnormality was found in the administration group after 4 hours of continuous observation. Four female rats and six male rats in the administration group showed perianal contamination on D1 after administration. From D3 after administration to the end of the observation period, all animals in the administration group showed no abnormality in activities and drinking water, no abnormal secretion in the mouth, eyes and nose, and no abnormality in hair color and respiration. The general health was in good condition.

During the experiment, the body weight of the rats in the solvent control group and the administration group increased gradually. There was no significant difference in body weight between female and male rats at different stages compared with solvent control group.

After the 14-day observation period, all animals were euthanized. Autopsy and general observation were carried out on all animals. No obvious abnormality was found in heart, liver, spleen, lung, kidney and other organs of all animals.

1.4 Conclusion

The results showed that the maximum tolerated dose (MTD) for ICR mice was more than 32 g/kg body weight, which was about 500 times of the proposed clinical dose.

In addition, Beagle dogs were used as experimental animals, and the same method as ICR mice was used for single dose administration. The results showed that there was no significant difference in respiratory function, blood pressure, body temperature, heart rate and ECG indexes between the experimental animals and the solvent control group within 4 hours after administration at dose of 0.6 g/kg, 1.2 g/kg and 2.4 g/kg (equivalent to 5 times, 10 times and 20 times of the recommended single dose for human).

7. Long Term Toxicity Test of the Composition of Example 2

The purpose of this experiment is to observe the nature and degree of possible toxic reactions in SD rats caused by repeated intragastric administration of the test substance as well as the development and recovery of the possible toxic reactions.

1.1 Experimental Animals

Methods: 120 SD rats, half male and half female, by Beijing Charles River Experimental Animal Technology Co., Ltd., wherein the female rats were about 7 weeks old, weighing 154-169 g at the time of receiving, and the male rats were about 6 weeks old, weighing 148-168 g at the time of receiving.

1.2 Experimental Reagents

The composition of Example 2 (HTL002) was accurately weighed and prepared into suspensions of different concentrations with 0.5% CMC Na solution before administration.

1.3 Experimental Procedure

The feeding conditions of experimental animals were as follows: room temperature 20-26° C., relative humidity 40-70%, minimum ventilation rate 15 times/h, light illumination: dark=12h: 12h. The animals were raised in a polypropylene rat group rearing box. The cage size was 545*395*200 mm$^3$, with 2-5 animals in each box. The animals were allowed to eat and move freely during the whole feeding process. The adaptation period was 6 days.

Grouping Methods: the animals were weighed before the experiment, and the male and female animals were randomly divided into groups. The experiment Methods: the animals were weighed before the experiment, and the male and female animals were randomly divided into four groups—solvent control group, low-dose group, medium-dose group and high-dose group, with 30 rats in each group, half male and half female.

TABLE 8

Toxicity test by repeated intragastric administration of test substance in SD rats

| Groups | Dose ($g \cdot kg^{-1}$) | Concentration ($mg \cdot ml^{-1}$) | Times of proposed human clinical dose | Number of animals ♀ | ♂ |
|---|---|---|---|---|---|
| I solvent control group | 0 | 0 | 0 | 15 | 15 |
| II low-dose group | 2.5 | 125 | 38.9 | 15 | 15 |
| III medium-dose group | 5 | 250 | 77.8 | 15 | 15 |
| IV high-dose group | 10 | 500 | 155.5 | 15 | 15 |

Administration scheme: the administration period was from 1 to 90 days, and the recovery period was from 91 to 121 days.

Route of administration: intragastric administration.

Dosage volume: 2 ml/100 g.

Frequency of administration: once a day.

Observation scheme: cage side observation was conducted before and after administration, and all animals were observed once a day. The observation contents included the appearance, hair, physical signs, behavior, respiratory state, gland secretion, animal posture, fecal characteristics, death, etc. Administration was continued for 90 days. At the end of administration, 79 animals (1 animal died accidentally) were killed. After 4 weeks of recovery, the remaining 40 animals were killed. The detection indexes included general condition, body weight, feed consumption, blood routine test, serum biochemistry, electrolyte, coagulation index, urine index, gross anatomy and histopathological examination.

1.4 Experimental Results:

1) Observation of General Physiological Indexes

During the experiment, the behavior, physical signs, fecal color and shape of the animals in the administration groups and the control group were normal, and no poisoning symptoms related to the administration were observed.

During the whole experiment, the body weight of male and female rats in each administration group and the control group increased continuously. There were no toxic changes in body weight and food intake in each group.

2) Clinicopathological Examination

At the end of administration, the content of total cholesterol (CHOL) in the low-, medium- and high-dose groups was higher than that in the solvent control group (16.7%-33.3% increase for female rats and 30.8%-61.5% increase for male rats). The change of CHOL was dose-dependent, suggesting that it might be related to administration, and male rats were more sensitive. However, at the end of the recovery period, the CHOL content returned to the level of the control group.

At the end of the administration and recovery period, the hematology, electrolyte, coagulation index, urine index and serum biochemical indexes of female and male rats in each administration group were not changed in toxicological significance compared with the solvent control group.

3) Histopathological Examination

Organ weight and organ index: at the end of administration, liver weight, liver index, kidney weight and kidney index of the low-, medium- and high-dose groups were higher than those of the solvent control group, and there was a certain dose-dependent effect. At the end of the recovery period, there were no significant changes in organ weight and index between the two groups.

Histopathology: at the end of administration, compared with the solvent control group, no pathological changes related to administration were found in the organs of the high-dose group. At the end of the recovery period, compared with the solvent control group, there was no cumulative or delayed toxic reaction related to administration in the high-dose group.

1.5 Conclusion

1) Under the condition of this experiment, SD rats were given the test substance (2.5, 5, 10 g·kg-1) by gavage for 90 days. The content of CHOL, the weight and index of liver and kidney in the three dose groups were higher than those in the solvent control group, and all indexes in the recovery period returned to normal. No toxic pathological changes related to administration were observed in all organs and tissues of SD rats treated with 10 g·kg-1 test substance by gavage for 90 days. After 4 weeks of drug withdrawal, there were no delayed or cumulative toxic pathological changes in the organs and tissues of the treated animals.

2) Under the conditions of this experiment, the HNSTD (highest non-severely toxic dose) in SD rats with repeated intragastric administration for 90 days was 10 g·kg-1, which was 156 times of the proposed clinical dose for human, indicating that the test substance was very safe.

The results of the above toxicity tests (acute toxicity test and long-term toxicity test) show that the composition of Example 2 was safe for experimental animals when administered at a single dose of about 500 times of the clinical intended dose, and it was still safe for the experimental animals when the long-term continuous administration was about 150 times of the proposed clinical dose, showing that the composition of Example 2 can not only be used as a drug for the treatment of chronic diseases (such as chronic heart failure) for a long time, but also can be used as a health care product for long-term consumption by normal people because it has no obvious side effects and has a preventive effect on thrombosis.

8. Effect of the Traditional Chinese Medicine Composition of Example 1 on Isoproterenol Induced Cardiac Function Injury in Rats This experiment is to verify the efficacy of the composition of Example 1 on the isoproterenol induced cardiac function injury model in rats.

1.1 Reagents and Instruments:

Test substance: the composition of Example 1 (HTL001), brown powder, soluble in distilled water.

Positive control: Compound Danshen Dripping Pills, from Tianjin Tasly Pharmaceutical Group Co., Ltd.

Pentobarbital sodium, from Sigma Company.

Isoflurane, from Hebei Jiupai Pharmaceutical Co., Ltd.

Isoproterenol, from Tokyo Chemical Industry Co., Ltd.

Instruments:

Visual Sonics Vevo770 high resolution small animal ultrasound imaging system, with 716 probe.

1.2 Experimental Animals

80 SD rats, male, weighing 240-300 g, provided by Beijing Charles River Experimental Animal Technology Co., Ltd., 1.3 Experimental Methods 1) Animal Grouping and Treatment The rats were weighed, and except for the normal control group (10 rats), isoproterenol (27 mg/kg, volume: 0.1 ml/100 g) was injected subcutaneously into the posterior neck for 4 consecutive days, once a day. The surviving animals were divided into model control group, Compound Danshen Dripping Pills group (150 mg/kg, positive control group), HTL001 high-dose group (1800 mg/kg), HTL001 medium-dose group (600 mg/kg) and HTL001 low-dose group (200 mg/kg), with 7 rats in each group. Rats were fasted for 12 hours before the experiment.

From the fourth day of modeling, the drug was given by gavage for 14 consecutive days.

2) Experimental Procedure

The cardiac function of the normal control group, model group and each administration group was examined by echocardiography. Before ultrasound imaging examination, the animals were anesthetized with gas. The concentration of isoflurane was 3% and the oxygen flow was controlled at 0.6 L/min. After anesthesia, the animals were fixed on the examination table in supine position, and the respiratory mask was connected. The anesthesia was maintained with 2% isoflurane and 0.6 L/min oxygen flow.

Echocardiographic analysis of the heart: the left ventricular short axis section near the sternum was taken and the M-mode ultrasonic motion curve was recorded at the level of mitral chordae tendineae. The left ventricular short axis fraction shortening (FS) and left ventricular ejection fraction (LVEF) were calculated. Each index was measured in three consecutive cardiac cycles (probe frequency 15 MHz), and the average value was taken.

1.4 Data Statistics

The data were expressed as Mean±SD and t-test was performed between groups.

1.5 Experimental Results

The experimental data are summarized in the table below.

TABLE 9

Effects of drugs on isoproterenol induced cardiac dysfunction in rats

| Groups | Number of animals #n | Dose (mg/kg) | LVEF (%) | FS (%) |
|---|---|---|---|---|
| Normal control group | 9 | — | 87.60 ± 3.20 | 59.53 ± 4.44 |
| Model group | 7 | — | 74.68 ± 2.48# | 45.50 ± 2.67# |
| Positive control group | 5 | 150 | 84.63 ± 6.17* | 56.71 ± 8.65* |
| HTL001 | 6 | 200 | 76.04 ± 7.20 | 46.73 ± 7.28 |
|  | 6 | 600 | 82.85 ± 6.68* | 54.26 ± 9.07* |
|  | 6 | 1800 | 81.10 ± 3.88* | 49.70 ± 5.88 |

Compared with the normal control group,
p < 0.001, compared with the model group,
*P < 0.05.

The results show that, compared with the normal control group, LVEF and FS in the model group were obviously damaged, while the positive control group had a significant recovery effect on LVEF and FS, indicating that the model was successful. The medium- and high-dose groups of HTL001 showed obvious recovery effect on LVEF, and the medium-dose group also had significant effect on FS.

1.6 Conclusion

The composition of Example 1 has protective effect on the cardiac function injury induced by isoproterenol at the dose of 600 mg/kg and 1800 mg/kg.

In addition, through similar experiments as experiments 2-7 described above, it has been confirmed that the composition of Example 1 had similar efficacy and safety with the composition of Example 2, including significant effects on myocardial systolic disorder, myocardial diastolic disorder, platelet aggregation thrombosis, myocardial ischemia, myocardial hypoxia, myocardial fatigue, etc., but the intensity of action was slightly lower in some pharmacodynamic aspects, which could be due to the relative decrease of the concentration of some active ingredients.

In addition, by administering the composition of Example 1 or Example 2 to some volunteers, it has been proved that the composition of Example 1 and the composition of Example 2 have significant effects on coronary heart disease, angina pectoris, heart failure, thrombosis, etc., and significantly improved the health of patients. In addition, it was also found that the composition of Example 1 had obvious effect in relieving shoulder and back pain symptoms caused by heart disease, which was likely due to the introduction of Bulbus Allii Macrostemonis and Cortex Eucommiae.

Although some specific embodiments have been described above, it is understandable to those skilled in the art that changes and combinations of forms and details can be made in the scope disclosed herein. It can be understood that, without departing from the wider scope disclosed herein and explained in accordance with the attached claims, various changes can be made to the adaptive description of different embodiments.

The invention claimed is:

1. A herbal medicine composition for the treatment of a cardiovascular or cerebrovascular disease, the active ingredients of which are composed of the following component 1) and component 2):
   1) an ethanol extract of 6-12 parts by weight of Rhizoma Chuanxiong and 5-10 parts by weight of Radix Curcumae; and
   2) an aqueous extract of 5-10 parts by weight of a combination of Radix Cyathulae and the extraction residue of said ethanol extraction of Rhizoma Chuanxiong and Radix Curcumae in component 1;
   Wherein the ethanol extract in component 1) and the aqueous extract in component 2) are separately concentrated to form two thick pastes, then the thick paste of component 1) and the thick paste of component 2) are combined, and the combined thick paste is spray dried to give the herbal medicine composition as a powder.

2. The herbal medicine composition according to claim 1, wherein the amounts of Rhizoma Chuanxiong and Radix Curcumae in component 1) are 6-12 parts and 6-8 parts, respectively, and wherein the amount of Radix Cyathulae in component 2) is 6-8 parts.

3. The herbal medicine composition according to claim 1, wherein the amounts of Rhizoma Chuanxiong and Radix Curcumae in component 1) are 8-10 parts and 6-8 parts, respectively, and wherein the amount of Radix Cyathulae in component 2) is 6-8 parts.

4. The herbal medicine composition according to claim 1, wherein the amounts of Rhizoma Chuanxiong and Radix Curcumae in component 1) are 9 parts and 7 parts, respectively, and wherein the amount of Radix Cyathulae in component 2) is 7 parts.

5. The herbal medicine composition according to claim 1, further comprising component 3): an aqueous extract of 5-10 parts by weight of Bulbus Allii Macrostemonis and 6-12 parts by weight of Cortex Eucommiae.

6. A method for preparing a herbal medicine composition according to claim 1, comprising:
   (1) weighing 6-12 parts of Rhizoma Chuanxiong and 5-10 parts of Radix Curcumae, extracting them with ethanol and concentrating the extraction liquid;
   (2) weighing 5-10 parts of Radix Cyathulae and mixing it with the extraction residue of step (1), extracting the mixture with water and concentrating the extraction liquid; and
   (3) combining the concentrates of step (1) and step (2) and then drying.

7. The method for preparing a herbal medicine composition according to claim 6, wherein 5-10 parts of Bulbus Allii Macrostemonis and 6-12 parts of Cortex Eucommiae are added in the step (2).

8. The method for preparing a Medicine herbal medicine composition according to claim 6, wherein:
   In Step (1), 50-70% ethanol is used and the extract is concentrated to a density of 1.05-1.150;
   In Step (2), the extract is concentrated to a density of 1.05-1.15g/I; and
   In Step (3), the drying is effected by spray drying.

9. An oral pharmaceutical preparation or health care product, comprising a herbal medicine composition according to claim 1 and a conventional medicinal adjuvant or auxiliary material.

10. A method of treating or preventing a cardiovascular or cerebrovascular disease or condition in a patient in need thereof, comprising administering to the patient an effective amount of a herbal medicine composition according to claim 1.

11. The method of treating or preventing a cardiovascular or cerebrovascular disease or condition in a patient in need thereof according to claim 10, wherein the cardiovascular or cerebrovascular disease or condition is selected from the group consisting of coronary heart disease, angina pectoris, myocardial infarction, thrombosis, stroke, systolic heart failure and diastolic heart failure.

12. The method of treating or preventing a cardiovascular or cerebrovascular disease or condition in a patient in need thereof according to claim 10, wherein the cardiovascular or cerebrovascular disease or condition is selected from the group consisting of myocardial systolic disorders, myocardial diastolic disorders, thrombosis, myocardial ischemia, myocardial hypoxia, cardiac muscle fatigue, or a cardiovascular or cerebrovascular disease caused by any of them.

13. The method of treating or preventing a cardiovascular or cerebrovascular disease or condition in a patient in need thereof according to claim 10, wherein the patient is a human patient and the composition is administered orally.

* * * * *